(12) United States Patent
Takagi et al.

(10) Patent No.: US 8,246,603 B2
(45) Date of Patent: Aug. 21, 2012

(54) CATHETER FOR CORONARY ARTERY AND ENGAGING METHOD THEREFOR

(75) Inventors: Ayumu Takagi, Shizuoka (JP); Hiroyoshi Ise, Shizuoka (JP); Daisuke Nakashima, Shizuoka (JP); Tetsuya Fukuoka, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 152 days.

(21) Appl. No.: 12/886,554

(22) Filed: Sep. 20, 2010

(65) Prior Publication Data

US 2011/0071503 A1  Mar. 24, 2011

(30) Foreign Application Priority Data

Sep. 18, 2009  (JP) .................................. 2009-216736
Jul. 21, 2010  (JP) .................................. 2010-164099

(51) Int. Cl.
*A61M 25/00* (2006.01)
(52) U.S. Cl. ........................................ 604/532; 604/523
(58) Field of Classification Search .................. 604/523, 604/532
See application file for complete search history.

(56) References Cited

U.S. PATENT DOCUMENTS

| 5,306,262 | A | * | 4/1994 | Weldon .......................... 604/532 |
| 5,445,625 | A | * | 8/1995 | Voda ............................. 604/532 |
| 5,876,385 | A | | 3/1999 | Ikari et al. |
| 5,916,209 | A | | 6/1999 | Mick |
| 5,957,911 | A | * | 9/1999 | Nesto ............................ 604/532 |
| 5,971,974 | A | * | 10/1999 | Keisz ............................ 604/523 |
| 6,066,126 | A | | 5/2000 | Li et al. |
| 6,273,881 | B1 | | 8/2001 | Kiemeneij |
| 6,355,026 | B1 | | 3/2002 | Mick |
| 6,620,150 | B2 | | 9/2003 | Kiemeneij |
| 6,723,083 | B2 | | 4/2004 | Kiemeneij |
| 2002/0103474 | A1 | * | 8/2002 | Voda ............................. 604/530 |
| 2004/0171996 | A1 | | 9/2004 | Kiemeneij |
| 2007/0250042 | A1 | | 10/2007 | Kiemeneij |

FOREIGN PATENT DOCUMENTS

| EP | 0 636 383 A1 | 2/1995 |
| JP | 8-10247 A | 1/1996 |
| JP | 8-215313 A | 8/1996 |
| JP | 3078261 B2 | 8/2000 |
| JP | 3563540 B2 | 9/2004 |

* cited by examiner

*Primary Examiner* — Kevin C Sirmons
*Assistant Examiner* — Emily Schmidt
(74) *Attorney, Agent, or Firm* — Kenealy Vaidya LLP

(57) ABSTRACT

A catheter for a coronary artery can include a distal end for being introduced into an opening of a coronary artery from an artery of an arm. The catheter can, include a catheter main body including a main body portion having a substantially linear shape in a natural state and a curved portion forming a portion extending from the main body portion to the distal end and having a curved shape in a natural state. The curved portion can include a first curve extending in a curved state from the main body portion, an intermediate portion extending from the first curve, a second curve extending from the intermediate portion and curved in a direction same as that of the first curve, and an extreme distal end portion of a substantially linear shape extending from the second curve. A method of using the catheter is also disclosed.

19 Claims, 17 Drawing Sheets

FIG. 9 Comparative Art

FIG. 10 Comparative Art

FIG. 11 Comparative Art

CATHETER FOR CORONARY ARTERY AND ENGAGING METHOD THEREFOR

This application claims the priority benefit under 35 U.S.C. §119 of Japanese Patent Application No. 2009-216736 filed on Sep. 18, 2009 and Japanese Patent Application No. 2010-164099 filed on Jul. 21, 2010, which are hereby incorporated in their entirety by reference.

BACKGROUND

1. Field

The disclosed subject matter relates to a catheter for a coronary artery for treating and imaging the heart or a peripheral tissue of the heart and an engaging method for the catheter.

2. Description of the Related Art

Conventionally, catheters for imaging a coronary artery include catheters of the Judkins type, the Amplatz type and so forth. Usually, these types of catheters are introduced from a femoral artery by the Seldinger method or a sheathing method to selectively image a coronary artery.

Also, many different treatments for a peripheral region of the heart using a catheter are available at present. For example, Percutaneous Transluminal Coronary Angioplasty (PTCA) of ischemic heart disease treatment using a catheter with a balloon is available. With regard to this treatment, in order to insert a treatment catheter into a target blood vessel safely and efficiently, the performance of the treatment catheter is important, and a guiding catheter which softens a reaction caused by the insertion and provides sufficient backup force to assist smooth introduction is often required. Shapes of such a guiding catheter can be similar to those of the Judkins type, the Amplatz type and so forth, which are similarly available as in the case of the imaging catheter for a coronary artery described above. Usually, a catheter having any of the above noted shapes is introduced from a femoral artery by the Seldinger method or the sheathing method to selectively assure introduction into a coronary artery, and then a treatment catheter such as a balloon catheter for PTCA is introduced into the inner face of the guiding catheter.

In the imaging or treatment processes for such conventional catheters, since the introduction site is a femoral region, in order to stanch a penetration site after the operation, complete bed rest may be required. Accordingly, urination, defecation, and eating and drinking may be required to be carried out in a supine position, and there is a problem in that discomfort, for example discomfort associated with lumbago, may be given to the patient. Further, where a catheter is introduced from a femoral region, there is the possibility that, even if the patient is in complete bed rest, bleeding may occur, and there is a problem that such bleeding may reach the retroperitoneum and cause further complications. Also urination is often difficult when a patient is in a supine position. In this instance, a problem may arise if a urethral catheter is being because there may be an increased possibility of acquiring a urinary tract infection.

As a method for eliminating or preventing the problems described above, introduction from an artery of an arm, particularly from a brachial artery or a radial artery, is considered effective. In particular, even when keeping a state in which a brachial penetrated site is stretched, the patient can walk immediately after the operation, and urination, defecation, and eating and drinking can be carried out in an ordinary manner without lumbago and so forth. Further, the possibility of bleeding from the retroperitoneum and/or contracting a urinary tract infection can be prevented. Taking such a situation as just described into consideration, a catheter for a coronary artery of a shape suitable for introduction from an arm is proposed in Japanese Patent Laid-Open Nos. Hei 8-10247 (Patent Document 1) and Hei 8-215313 (Patent Document 2), and Japanese Patent Nos. 3,078,261 (Patent Document 3) and 3,563,540 (Patent Document 4).

SUMMARY

Incidentally, when viewing a plane in which the aorta of a human being exists and the aorta and the left and right coronary arteries are viewed from the front side of the aorta of a human being, the opening of the left coronary artery is positioned a little towards the front side with respect to the plane while the opening of the right coronary artery is positioned a little to the interior side with respect to the plane. However, the catheters for a coronary artery disclosed in Patent Documents 1 to 4 specified above are not configured in a shape that would take the positional relationship of the aorta and the openings of the left and right coronary arteries into consideration. Thus, in order to allow quicker and easier introduction of the distal end of a catheter into the opening of a coronary artery, development of a further improved catheter for a coronary artery is demanded.

According to an aspect of the presently disclosed subject matter, a catheter for a coronary artery can be configured with a distal end that can be introduced into the opening of a coronary artery through an artery of an arm and can be introduced into the opening of a coronary artery rapidly, reliably and easily. The disclosed subject matter includes an engaging method for the catheter for a coronary artery.

According to another aspect of the disclosed subject matter, there is provided a catheter for a coronary artery having a distal end configured to be introduced into an opening of a coronary artery from an artery of an arm, including a catheter main body having a main body portion with a substantially linear shape in a natural state and a curved portion forming a portion extending from the main body portion to the distal end and having a curved shape in a natural state, the curved portion including a first curve extending in a curved state from the main body portion, an intermediate portion extending from the first curve, a second curve extending from the intermediate portion and curved in a direction same as that of the first curve, and an extreme distal end portion of a substantially linear shape extending from the second curve, the first curve, intermediate portion and second curve existing in a substantially same plane, the extreme distal end portion extending, when the curved portion is positioned on the upper side of the main body portion and is viewed from a point of view at which the curved portion is positioned on the right side of the main body portion, substantially linearly and obliquely to the interior side (back side) from the plane in which the first curve, intermediate portion and second curve exist.

In the above-described catheter for a coronary artery, when the curved portion is viewed from such a particular point of view as described above, the extreme distal end portion of the curved portion extends substantially linearly and obliquely toward the interior side in such a manner as to deviate from the plane in which the first curve, intermediate portion and second curve exist, that is, toward the rear side (back side) of the plane. Therefore, the extreme distal end portion is shaped so as to be suitable for introduction of the catheter distal end into the openings (ostiums) of the left and right coronary artery. In particular, when viewing a plane in which the aorta of a human being exists, that is, the plane in which the aorta ascendens and the brachiocephalic artery of a human being exists, and the aorta and the left and right coronary arteries are viewed from the front side of the aorta, the opening of the left coronary artery is positioned in a slightly displaced relationship to a front side from the plane. Meanwhile, the opening of the right coronary artery is positioned in a slightly displaced relationship to an interior side with respect to the plane. Thus, with the catheter for a coronary artery, since the extreme distal end portion extends obliquely with respect to the plane in which the first curve, intermediate portion and second curve exist, as described above, when the curved portion is inserted in the aorta, even if the first curve, intermediate portion and second curve are positioned in the plane in which the aorta exists or in a plane parallel to the aorta plane, the extreme distal end portion is directed to the left coronary artery opening side or the right coronary artery opening side. Therefore, introduction of the extreme distal end portion into the left and right coronary artery openings can be carried out rapidly, reliably and easily.

When the extreme distal end portion engages with the opening of the coronary artery, the first curve can contact with an inner wall of the aorta on the opposite side to the opening of the coronary artery, and the length over which the first curve and the inner wall of the aorta contact with each other can be smaller than 10 mm.

In the catheter for a coronary artery, when the first curve engages with the inner wall of the aorta to carry out backup support, where the length over which the first curve and the inner wall of the aorta contact with each other is smaller than 10 mm, the direction of the curved portion can be changed readily around a fulcrum provided by the first curve. Accordingly, the direction of the catheter distal end, that is, of the extreme distal end portion of the catheter, can be changed readily. Therefore, the operability of the catheter for a coronary artery can be improved.

The curved portion can be shaped such that, when the extreme distal end portion engages with the opening of the coronary artery, the axial line of the opening of the coronary artery and the axial line of the extreme distal end portion are inclined relative to each other.

In the catheter for a coronary artery, the extreme distal end portion is prevented from excessively advancing to the interior side of the coronary artery and can be engaged at an appropriate position with the opening of the coronary artery.

The curved portion can be configured from only the four elements of the first curve, intermediate portion, second curve and extreme distal end portion.

In the catheter for a coronary artery, when the catheter is circulated in a blood vessel, the resistance in the blood vessel can be lower than resistance associated with an alternative catheter which has a greater number of curves, and the passing property of a device for treatment in the catheter is good. Further, it is easy to apply torque to the catheter.

The curved portion can be shaped so as to be selectively engageable with an opening of the left coronary artery and an opening of the right coronary artery.

In the catheter for a coronary artery, since the curved portion can be engaged with the left and right coronary arteries, when the target of engagement is to be changed over from the opening of the left coronary artery to the opening of the right coronary artery, if the curved portion is rotated by 180°, then the extreme distal end portion is directed to the opening of the right coronary artery. On the contrary, when the target of engagement is to be changed over from the opening of the right coronary artery to the opening of the left coronary artery, if the curved portion is rotated by 180°, then the extreme distal end portion is directed to the opening of the left coronary artery. Accordingly, when the target of engagement is changed over between the opening of the left coronary artery and the opening of the right coronary artery, the extreme distal end portion can be engaged readily with the opening of the left or right coronary artery.

According to another aspect of the disclosed subject matter, there is provided a catheter for a coronary artery for being engaged with an opening (ostium) of a coronary artery, the catheter for a coronary artery having a distal end configured to be introduced into the opening (ostium) of the coronary artery from an artery of an arm, including a catheter main body including a main body portion having a substantially linear shape in a natural state and a curved portion forming a portion extending from the main body portion to the distal end and having a curved shape in a natural state, the curved portion including a first curve extending in a curved state from the main body portion, an intermediate portion extending from the first curve, a second curve extending from the intermediate portion and curved in a direction same as that of the first curve, and an extreme distal end portion of a substantially linear shape extending from the second curve, the first curve, intermediate portion and second curve existing in a substantially same plane, the extreme distal end portion extending, when the curved portion is positioned on the upper side of the main body portion and is viewed from a point of view at which the curved portion is positioned on the right side of the main body portion, substantially linearly and obliquely to the interior side from the reference plane in which the first curve, intermediate portion and second curve exist, the curved portion being shaped so as to be selectively engageable with an opening (ostium) of the left coronary artery and an opening (ostium) of the right coronary artery, the catheter for a coronary artery being configured such that the extreme distal end portion is engaged with one of the opening (ostium) of the left coronary artery and the opening (ostium) of the right coronary artery, that the extreme distal end portion is disengaged from the one of the opening (ostium) of the left coronary artery and the opening (ostium) of the right coronary artery, that the extreme distal end portion is rotated along a wall of the aorta in a direction in which the extreme distal end portion forms a smaller angle with respect to the wall of the aorta, and that the extreme distal end portion is engaged with the other of the opening (ostium) of the left coronary artery and the opening (ostium) of the right coronary artery.

According to a further aspect of the disclosed subject matter, there is provided an engaging method for a catheter for a coronary artery for being engaged with an opening of a coronary artery, the catheter for a coronary artery having a distal end for being introduced into the opening of the coronary artery from an artery of an arm, the catheter for a coronary artery including a catheter main body including a main body portion having a substantially linear shape in a natural state and a curved portion forming a portion extending from the main body portion to the distal end and having a curved shape in a natural state, the curved portion including a first curve extending in a curved state from the main body portion, an intermediate portion extending from the first curve, a second curve extending from the intermediate portion and curved in a direction same as that of the first curve, and an extreme distal end portion of a substantially linear shape extending from the second curve, the first curve, intermediate portion and second curve existing in a substantially same plane, the extreme distal end portion extending, when the curved portion is positioned on the upper side of the main body portion and is viewed from a point of view at which the curved portion is positioned on the right side of the main body portion, substantially linearly and obliquely to the interior side from the reference plane in which the first curve, intermediate portion and second curve exist, the curved portion being shaped so as to be selectively engageable with an opening of the left coronary artery and an opening of the right coronary artery, the engaging method including engaging the extreme distal end portion with one of an opening of the left coronary artery and an opening of the right coronary artery, disengaging the extreme distal end portion from the one of the opening of the left coronary artery and the opening of the right coronary artery, rotating the extreme distal end portion along a wall of the aorta in a direction in which the extreme distal end portion forms a smaller angle with respect to the wall of the aorta, and engaging the extreme distal end portion with the other of the opening of the left coronary artery and the opening of the right coronary artery.

In the catheter for a coronary artery and the engaging method, the extreme distal end portion of the catheter for a coronary artery can extend substantially linearly and obliquely toward the interior side in such a manner as to deviate from the plane in which the first curve, intermediate portion and second curve exist, that is, toward the rear side (back side) of the plane. Therefore, when the extreme distal end portion is to be moved from one to the other of the opening of the left coronary artery to the opening of the right coronary artery, it rotates along the inner wall of the aorta in a state in which it contacts at an angle smaller than the right angle with the wall of the aorta. Therefore, the catheter for a coronary artery is less likely to damage the wall of the aorta in comparison with an alternative catheter wherein the extreme distal end portion exists in the same plane as that in which the other portions of the curved portion exist.

In the catheter for a coronary artery and the engaging method, the intermediate portion can have a substantially linear shape, and the angle defined by the extreme distal end portion and the reference plane can be set to 8 to 35°.

Where the inclination angle of the extreme distal end portion is set in this manner, when the extreme distal end portion of the catheter for a coronary artery wherein the intermediate portion has a substantially linear shape is to be moved from one to the other of the opening of the left coronary artery and the opening of the right coronary artery, it can be rotated along the inner wall of the aorta without being caught strongly by the inner wall of the aorta.

In the catheter for a coronary artery and the engaging method, the intermediate portion can have a substantially linear shape, and the angle defined by the extreme distal end portion and the reference plane can be set to 10 to 30°.

Where the inclination angle of the extreme distal end portion is set in this manner, when the extreme distal end portion of the catheter for a coronary artery wherein the intermediate portion has a substantially linear shape is to be moved from one to the other of the opening of the left coronary artery and the opening of the right coronary artery, it can be rotated smoothly along the inner wall of the aorta and besides engagement of the extreme distal end portion with the opening of the coronary artery can be carried out smoothly.

In the catheter for a coronary artery and the engaging method, the intermediate portion can be shaped so as to be curved in a direction same as that of the first curve, and the angle defined by the extreme distal end portion and the reference plane can be set to 7 to 36°.

Where the inclination angle of the extreme distal end portion is set in this manner, when the extreme distal end portion of the catheter for a coronary artery wherein the intermediate portion has a substantially linear shape is to be moved from one to the other of the opening of the left coronary artery and the opening of the right coronary artery, it can be rotated along the inner wall of the aorta without being caught strongly by the inner wall of the aorta.

In the catheter for a coronary artery and the engaging method, the intermediate portion can be shaped so as to be curved in a direction same as that of the first curve, and the angle defined by the extreme distal end portion and the reference plane can be set to 11 to 29°.

Where the inclination angle of the extreme distal end portion is set in this manner, when the extreme distal end portion of the catheter for a coronary artery wherein the intermediate portion has a substantially linear shape is to be moved from one to the other of the opening of the left coronary artery and the opening of the right coronary artery, it can be rotated smoothly along the inner wall of the aorta and besides engagement of the extreme distal end portion with the opening of the coronary artery can be carried out smoothly.

With the catheters for a coronary artery, since the extreme distal end portion can be inclined with respect to the plane in which the first curve, intermediate portion and second curve exist so that the extreme distal end portion is directed to the opening of the left coronary artery or the opening of the right coronary artery when the curved portion of the catheter main body is introduced into the aorta, introduction of the catheter distal end into the opening of the left or right coronary artery can be carried out rapidly, reliably and easily.

With the engaging method for a catheter for a coronary artery, when the target of engagement is changed over from one to the other of the openings of the left and right coronary arteries, the extreme distal end portion moves smoothly in a state in which it forms an angle smaller than a right angle with respect to the wall of the aorta. Therefore, the extreme distal end portion is less likely to damage the wall of the aorta.

The above and other features, characteristics, and advantages of the disclosed subject matter will become apparent from the following description and the appended claims, taken in conjunction with the accompanying drawings in which like parts or elements are denoted by like reference symbols.

DETAILED DESCRIPTION OF EXEMPLARY EMBODIMENTS

In the following description, examples of a catheter for a coronary artery and an engaging method of the same according to embodiments of the disclosed subject matter are described with reference to the accompanying drawings.

Figure 1:
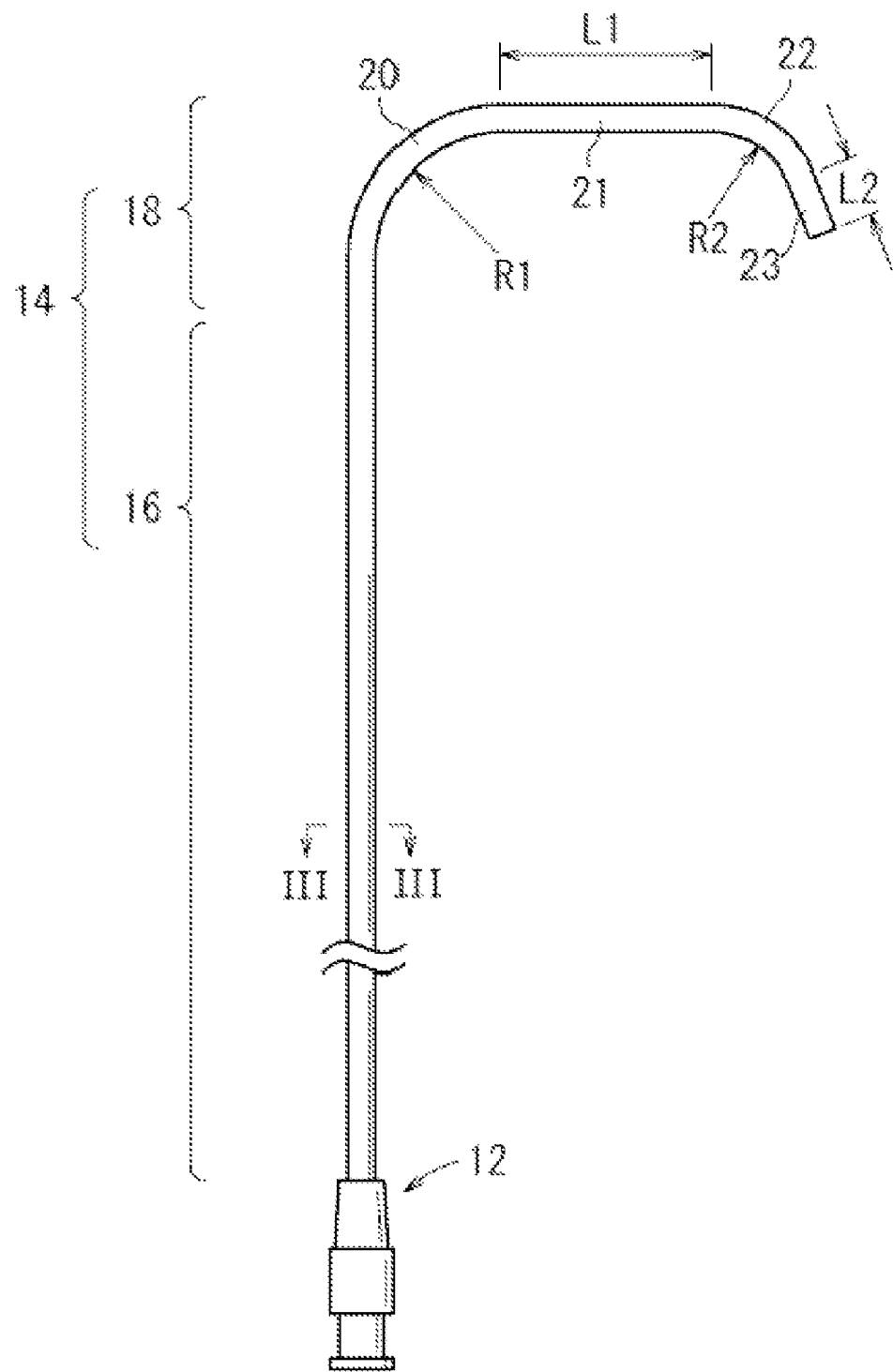
FIG. 1 is a partial plan view showing an embodiment of a catheter for a coronary artery made in accordance with principles of the disclosed subject matter.

FIG. 1 shows a catheter 10 for a coronary artery (hereinafter sometimes referred to as catheter 10) according to an embodiment of the disclosed subject matter. The catheter 10 shown is configured to introduce the distal end thereof into the left coronary artery opening or the right coronary artery opening from an artery of an arm, particularly from an artery of the right arm.

Referring to FIG. 1, the catheter 10 can include a catheter main body 14 of a hollow structure having flexibility, and a hub 12 formed at the proximal end of the catheter main body 14. The hub 12 functions as an injection port for injecting contrast medium or the like or as an insertion port for a device for treatment.

In order to allow the catheter 10 to be introduced from a brachial artery of a human being, for example, from a radial artery, the outer diameter of the catheter main body 14 can be set to 2.7 mm or less (possibly equal to or less than 2.1 mm) over the overall length thereof. The catheter 10 introduced from an arm passes the radial artery and reaches the aorta ascendens.

The catheter main body 14 has a main body portion 16 having a substantially linear shape in a natural state, and a curved portion 18 extending from the main body portion 16 to form a portion to the distal end and having a curved shape in a natural state. Here, the "natural state" signifies a state in which no external force is applied, and the term is used in the following description so as to have similar meaning.

The main body portion 16 has a substantially linear shape in a natural state. The length of the main body portion 16 is not particularly limited, but can be 400 to 1,000 mm, for example.

The curved portion 18 can include a first curve 20 extending in a curve from the main body portion, an intermediate portion 21 extending from the first curve 20, a second curve 22 extending from the intermediate portion 21 and curved in the same direction as the first curve 20, and a substantially linear extreme distal end portion 23 extending from the second curve 22. The first curve 20, intermediate portion 21 and second curve 22 can exist in substantially the same plane.

The first curve 20 exhibits a curved shape, that is, a shape curved in the clockwise direction in FIG. 1 from the main body portion 16, in a natural state thereof. In the present embodiment, the first curve 20 can be configured such that, in a natural state thereof, a radius R1 of curvature thereof is 15 to 25 mm and the angle thereof, which is a range over which the first curve 20 extends around the center of the curvature, is 70 to 90°. In the configuration example shown in FIG. 1, the radius R1 of curvature of the first curve 20 is set to 15 mm and the angle of the first curve 20 is set to 88°.

The intermediate portion 21 can have a substantially linear shape in a natural state thereof. The length L1 of the intermediate portion 21 can be set such that, when the extreme distal end portion 23 is engaged with the left coronary artery opening, the first curve 20 contacts with the inner wall of the aorta on the opposite side to the left coronary artery opening, that is, with the right wall of the aorta ascendens. Also, the length L1 of the intermediate portion 21 can be set such that, when the extreme distal end portion 23 is engaged with the right coronary artery opening, the first curve 20 contacts with the inner wall of the aorta on the opposite side to the right coronary artery opening, that is, with the left wall of the aorta ascendens. Consequently, the first curve 20 can contact with certainty with the inner wall of the aorta and the extreme distal end portion 23 can be prevented from being disengaged from the left coronary artery opening or the right coronary artery opening. From such a point of view as just described, the length L1 of the intermediate portion 21 can be set to approximately 10 to 40 mm, which can be a length with which the intermediate portion 21 extends from one to the other wall face of the aorta. In the configuration example shown in FIG. 1, the length L1 of the intermediate portion 21 is set to 20 mm.

The second curve 22 exhibits a curved shape in a natural state thereof, that is, a shape curved in the clockwise direction from the main body portion 16 in FIG. 1. In the present embodiment, the second curve 22 can be set such that, in a natural state thereof, the radius R2 of curvature thereof is 5 to 10 mm and the angle is 60 to 65°. In the configuration example shown in FIG. 1, the radius R2 of curvature of the second curve 22 is set to 8 mm, and the angle of the second curve 22 is set to 65°.

The extreme distal end portion 23 can have a substantially linear shape in a natural state thereof. The length L2 of the extreme distal end portion 23 can be set to such a degree that the extreme distal end portion 23 does not excessively enter the left coronary artery opening or the right coronary artery opening but can be inserted and self-retained with certainty, and for example can be set particularly to approximately 5 to 50 mm. In the configuration example shown in FIG. 1, the length L2 of the extreme distal end portion 23 is set to 7 mm. The curved portion 18 can be shaped such that, when the extreme distal end portion 23 is positioned in the left coronary artery opening, it is inclined with respect to the axial direction of the left coronary artery opening.

The curved portion 18 can be configured only from the four factors of the first curve 20, intermediate portion 21, second curve 22 and extreme distal end portion 23. By the configuration as just described, when the catheter 10 is circulated in a blood vessel, the intra-blood vessel resistance can be lower than that of a catheter which has a greater number of curves, and is good in passing performance with respect to a device for treatment passing in the catheter 10. Further, it is easy to apply torque to the catheter 10.

The catheter 10 having the shape set in such a manner as described above can selectively engage the extreme distal end portion 23 with any of the left coronary artery opening and the right coronary artery opening.

Figure 2:
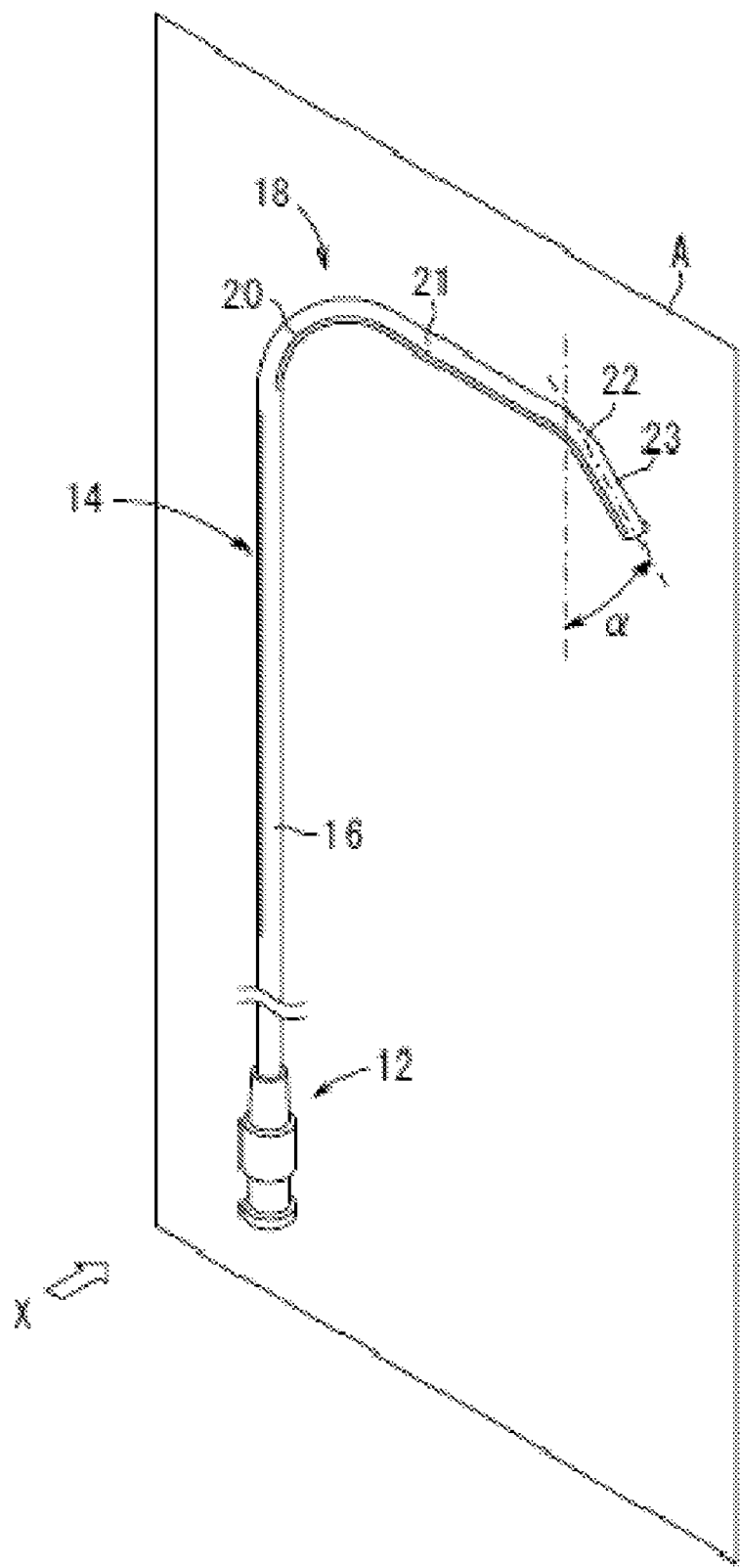
FIG. 2 is a partial perspective view showing a three-dimensional shape of the catheter for a coronary artery of FIG. 1.

FIG. 2 is a partial perspective view, showing a three-dimensional shape of the catheter 10 according to the embodiment of FIG. 1. Referring to FIG. 2, a plane A in which the first curve 20, intermediate portion 21, and second curve 22 exist is assumed. Further, if it is assumed that the curved portion 18 is positioned on the upper side of the main body portion 16 and is viewed from a point of view at which the curved portion 18 is positioned on the right side of the main body portion 16, that is, from a point of view from the direction of arrow X in FIG. 2, then the extreme distal end portion 23 extends substantially linearly in an oblique direction to the interior side (back side) from the plane A, that is, in such a manner as to deviate from the plane A. In other words, the extreme distal end portion 23 can extend substantially linearly and obliquely away from a point of a viewer when the catheter 10 is viewed from a point of view at which the curved portion is positioned on a right side and at a top of the main body portion (i.e., the extreme distal end portion 23 can extend into the paper as viewed in FIG. 2). The inclination angle α of the extreme distal end portion 23 with respect to the plane A can be set from 10 to 30°, and for example can be 16 to 20°. In the configuration example shown in FIG. 2, the inclination angle α is set to 16°. If the inclination angle α is smaller than 10°, then the extreme distal end portion 23 exists in a plane very proximate to the plane A and may be inserted into the coronary artery. If the inclination angle α is greater than the angle of 30°, then the extreme distal end portion 23 may not be engaged with the coronary artery, and if the extreme distal end portion 23 is inserted forcibly, then it may damage the blood vessel wall by repulsive force.

Figure 3:
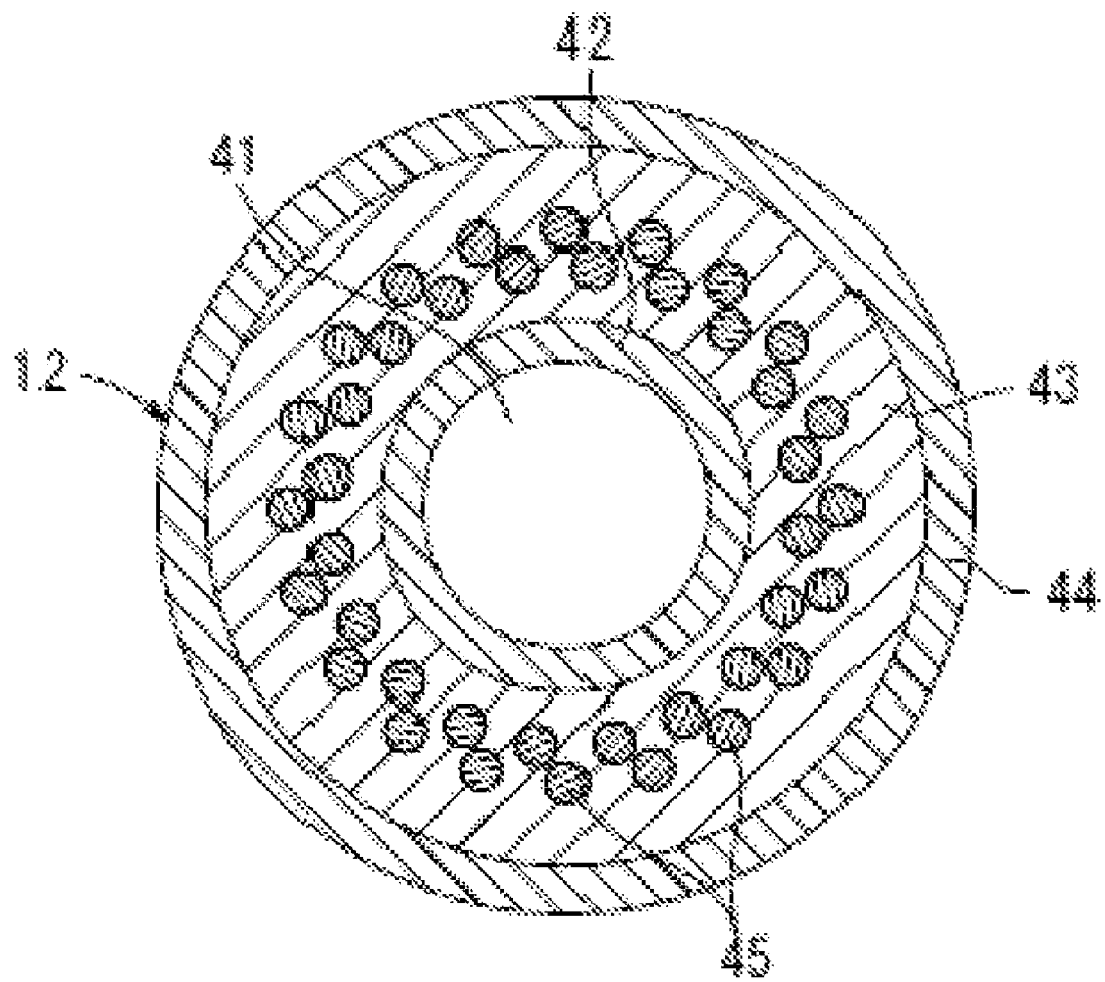
FIG. 3 is a sectional view of the catheter for a coronary artery taken along line III-III of FIG. 1.

FIG. 3 is a sectional view of the catheter 10 for a coronary artery taken along line III-III of FIG. 1. Referring to FIG. 3, a lumen 41 is formed at a substantially central location of the catheter main body 14. The lumen 41 is open at the distal end of the catheter main body 14.

Further, the catheter main body 14 can be structured such that an inner layer 42, an intermediate layer 43 and an outer layer 44 are laminated concentrically from the inner side toward the outer side. Since the catheter main body 14 can be configured in this manner, there are advantages in that a bend of the catheter main body 14 can be prevented and that the component materials, compounding ingredients, surface properties and so forth of the layers can be changed such that advantages associated with each of them can be shared.

As the component materials of the inner layer 42, intermediate layer 43 and outer layer 44, a polyamide-based resin such as nylon 11, nylon 12 or nylon 6, a polyester-based polyamide-based resin such as, for example, Grilax (trade name, by DIC), a polyether-based polyamide resin such as, for example, Pebax (trade name, by Atochem), polyurethane, an ABS resin, a polyester elastomer resin, polyurethane elastomer resin and a fluorocarbon-based resin such as PFA, PTFE or ETFE, or other known material for use in catheters, can be used. Particularly if an ABS resin or nylon is used as the component material(s) of the inner layer 42, intermediate layer 43 and outer layer 44, a suitable strength can be provided to the curved portion 18. Further, if a fluorocarbon-based resin, such as PTFE, is used for the inner layer 42, then the operability of a guide wire 48 (refer to FIG. 5) for being inserted into the lumen 41 or a catheter for treatment is improved. It is to be noted that, since insertion of the catheter 10 is carried out while the position thereof is being confirmed under radiographic guidance, a radiopaque material such as, for example, barium sulfate, bismuth oxide, tungsten, or other known radiopaque material can be used or compounded in a material from which the catheter main body 14 is formed.

Further, although the thickness of the inner layer 42, intermediate layer 43 and outer layer 44 is not particularly limited, in the example shown, the inner layer 42 has a thickness smaller than that of the intermediate layer 43 and the outer layer 44. Further, the inner layer 42, intermediate layer 43 and outer layer 44 can be adhered to each other by a suitable bonding agent or fusion bonded to each other by heat or else can be molded integrally by coating molding or the like. It is to be noted that the outer layer 44 and the intermediate layer 43 may be formed as a first layer (not shown) made of the same resin.

In the intermediate layer 43, a metal mesh 45 having a role as a reinforcing member can be embedded over an overall periphery thereof. The metal mesh 45 may be provided in a contacting relationship with the outer surface of the inner layer 42. The metal mesh 45 can be embedded, in the longitudinal direction of the catheter 10, over a substantially overall length of the catheter main body 14 except in a predetermined length from the distal end of the catheter main body 14. The position of the end of the metal mesh 45 can be within a range of 0.5 to 150 mm, for example from 1 to 100 mm, from the distal end of the catheter main body 14.

By embedding such a metal mesh 45 as just described, it is possible to prevent bending of the catheter main body 14 and to improve the torque transferability when the catheter main body 14 is rotated. The cross section of a wire which is configured with the metal mesh 45 may be a circular shape, a rectangular shape, a substantially elliptical shape, or other known shape used for a catheter.

It is to be noted that the reason why the metal mesh 45 is not necessarily embedded over the predetermined length from the distal end of the catheter main body 14 is that, if the metal mesh 45 extends to the tip end of the catheter main body 14, then there is the possibility that the blood vessel wall may be damaged by the distal end of the catheter and, depending upon the material, if the metal mesh 45 extends to the neighborhood of the distal end of the catheter, then the catheter may become so hard that the distal end of the catheter becomes liable to enter the left ventricle without entering the opening of the coronary artery by a technique hereinafter described. The distal end of the catheter 10 is not typically configured such that it is used in such a state that it reaches the left ventricle or the left atrium.

It is to be noted, however, that, if the metal mesh 45 does not exist at a portion of a length exceeding 150 mm from the distal end of the catheter main body 14, then the torque transferability mentioned hereinabove may not sometimes be obtained.

It is to be noted that the length of the portion at which the metal mesh 45 is not provided can be determined suitably depending upon the material, the difference between the inner and outer diameters, that is, the total thickness of the inner layer 42, intermediate layer 43 and outer layer 44, and so forth of the catheter main body 14. For example, as the difference between the inner and outer diameters of the catheter main body 14 increases, or as the elastic force of the material increases, the length of the portion over which the metal mesh 45 is not provided can be increased.

As a particular example of the metal mesh 45, a mesh formed from stainless steel, stainless steel spring wires, tungsten, Ni—Ti, wires of a small diameter such as carbon fibers, or other known meshes, may be used, and the line diameter can be, for example, approximately 0.01 to 0.2 mm.

The catheter 10 according to the embodiment of FIG. 1 can be basically configured in such a manner as described above, and operation and effects of the catheter 10 are described below. The following description is directed to an example of a method of use of the catheter 10 wherein the catheter 10 is used as a guiding catheter which is used together with a treatment catheter.

Figure 4:
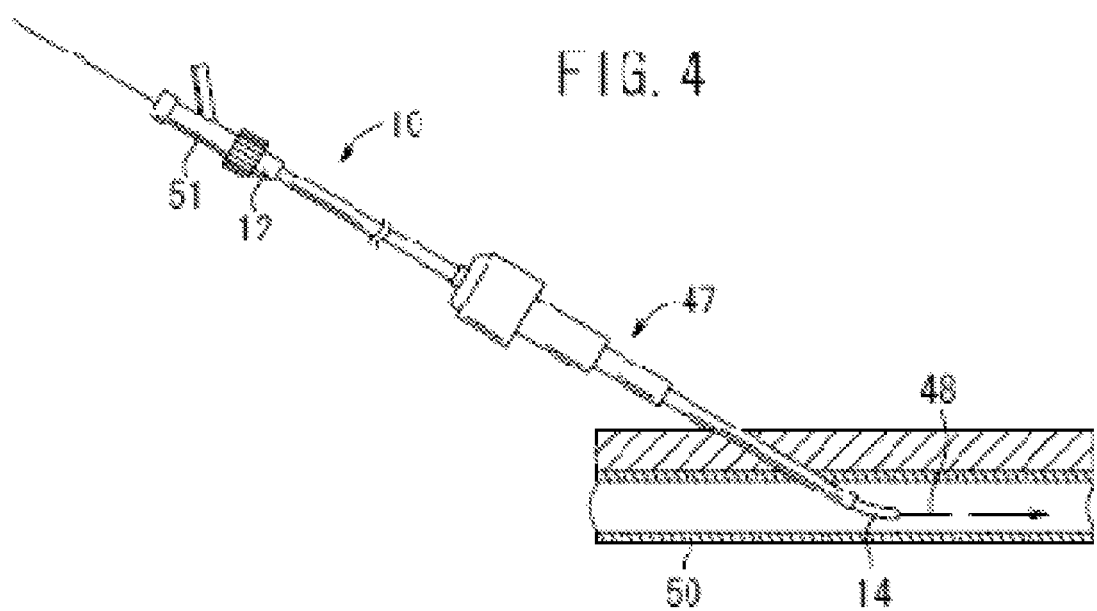
FIG. 4 is a schematic view illustrating an exemplary blood vessel introduction method for the catheter for a coronary artery of FIG. 1.

Referring to FIG. 4, a brachial artery or radial artery 50 is punctured with a catheter introducer 47 by the Seldinger method, and the catheter 10 in a state in which the guide wire 48 is inserted is inserted into the catheter introducer 47. Then, in a state in which the guide wire 48 precedes to the distal end of the catheter main body 14, the distal end of the catheter main body 14 is inserted into the brachial artery or radial artery 50 from an opening at the distal end of the catheter introducer 47.

Figure 5:
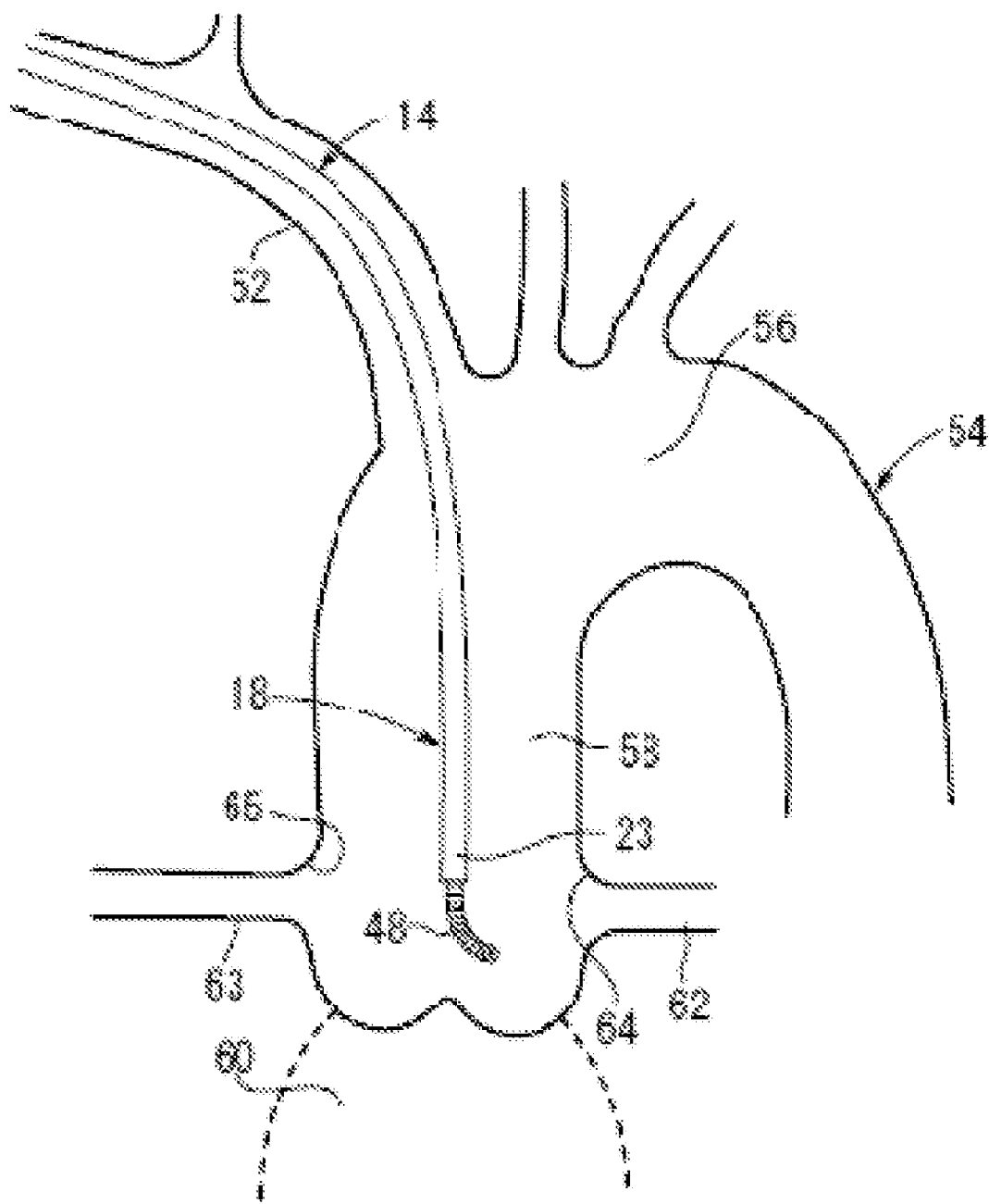
FIG. 5 is a schematic view showing the catheter of FIG. 1 in a state wherein the distal end of the catheter is introduced to a position in the proximity of the opening of the left or right coronary artery by a guide wire.

Then, the catheter 10 and the guide wire 48 are fed gradually in the direction indicated by an arrow mark in FIG. 4 so that they are inserted into the aorta ascendens 58 through the aortic arch 56 of the aorta 54 as shown in FIG. 5. Thereupon, operation of a suitable combination of insertion and removal of the guide wire 48 and back and forth movement and rotation of the catheter 10 is carried out so that the distal end of the catheter main body 14 may pass through a bent portion of a blood vessel.

As shown in FIG. 5, the catheter 10 introduced into the aorta ascendens 58 from the brachiocephalic artery 52 is introduced to the neighborhood of the left ventricle 60. At this time, since the curved portion 18 of the catheter main body 14 is stretched by the guide wire 48 inserted in the lumen 41, it exhibits a substantially linear shape.

Thereafter, if the guide wire 48 is pulled off from the catheter main body 14, then the curved portion 18 restores to its original curved shape. By repulsive force generated by such shape restoration, the catheter distal end is directed to and inserted into the opening of the left coronary artery 62, that is, directed to and inserted into the left coronary artery opening 64. Consequently, a state in which the catheter distal end, that is, the extreme distal end portion 23, engages with the left coronary artery opening 64 is established. It is to be noted that, if the catheter distal end is not inserted in the left coronary artery opening 64, then if light rotation is applied to a proximal end portion of the catheter 10 suitably, then the extreme distal end portion 23 can be inserted readily into the left coronary artery opening 64.

In the state in which the extreme distal end portion 23 engages with the left coronary artery opening 64, the first curve 20 contacts with the aorta ascendens right wall 66 positioned on the opposite side to the left coronary artery opening 64 such that backup support is carried out by the first curve 20. Since the catheter main body 14 is shaped in such a manner as described above, high backup force is exerted. By this backup force, the curved portion 18 of the catheter main body 14 is fixed well to the aorta ascendens 58, and consequently, the extreme distal end portion 23 is less likely to disengage from the left coronary artery opening 64.

With the catheter 10 according to the exemplary embodiment of FIG. 1, when the curved portion 18 is viewed from a particular point of view as shown in FIG. 2, since the extreme distal end portion 23 of the curved portion 18 extends substantially linearly from the plane A, in which the first curve 20, intermediate portion 21 and second curve 22 exist, obliquely to the interior side, it is shaped suitably for introduction of the extreme distal end portion 23 into the left coronary artery opening 64. In particular, when the plane A in which the aorta 54 of a human being exists, that is, the plane in which the aorta ascendens 58 and the brachiocephalic artery 52 of a human being exist, is assumed and the aorta 54 and the left coronary artery opening 64 are viewed from the front side of the aorta 54, the left coronary artery opening 64 is positioned in a slightly displaced relationship to the front side from the plane A in which the aorta 54 exists. Thus, with the catheter 10, since the extreme distal end portion 23 extends in a direction inclined with respect to the plane A in which the first curve 20, intermediate portion 21 and second curve 22 exist, when the curved portion 18 is inserted in the aorta 54, even if the first curve 20, intermediate portion 21 and second curve 22 are positioned in the plane in which the aorta 54 exists or in a plane parallel to the plane, the extreme distal end portion 23 is directed to the left coronary artery opening 64 side. Therefore, introduction of the extreme distal end portion 23 into the left coronary artery opening 64 can be carried out rapidly, reliably and easily.

In the catheter 10, the first curve 20 can be shaped such that the contact length H1 thereof with the inner wall of the aorta is smaller than 10 mm. If the contact length between the first curve 20 and the inner wall of the aorta is smaller than 10 mm, then the direction of the curved portion 18 can be changed readily around a fulcrum provided by the first curve 20, and accordingly, the direction of the catheter distal end, that is, of the extreme distal end portion 23, can be readily changed.

Figure 6:
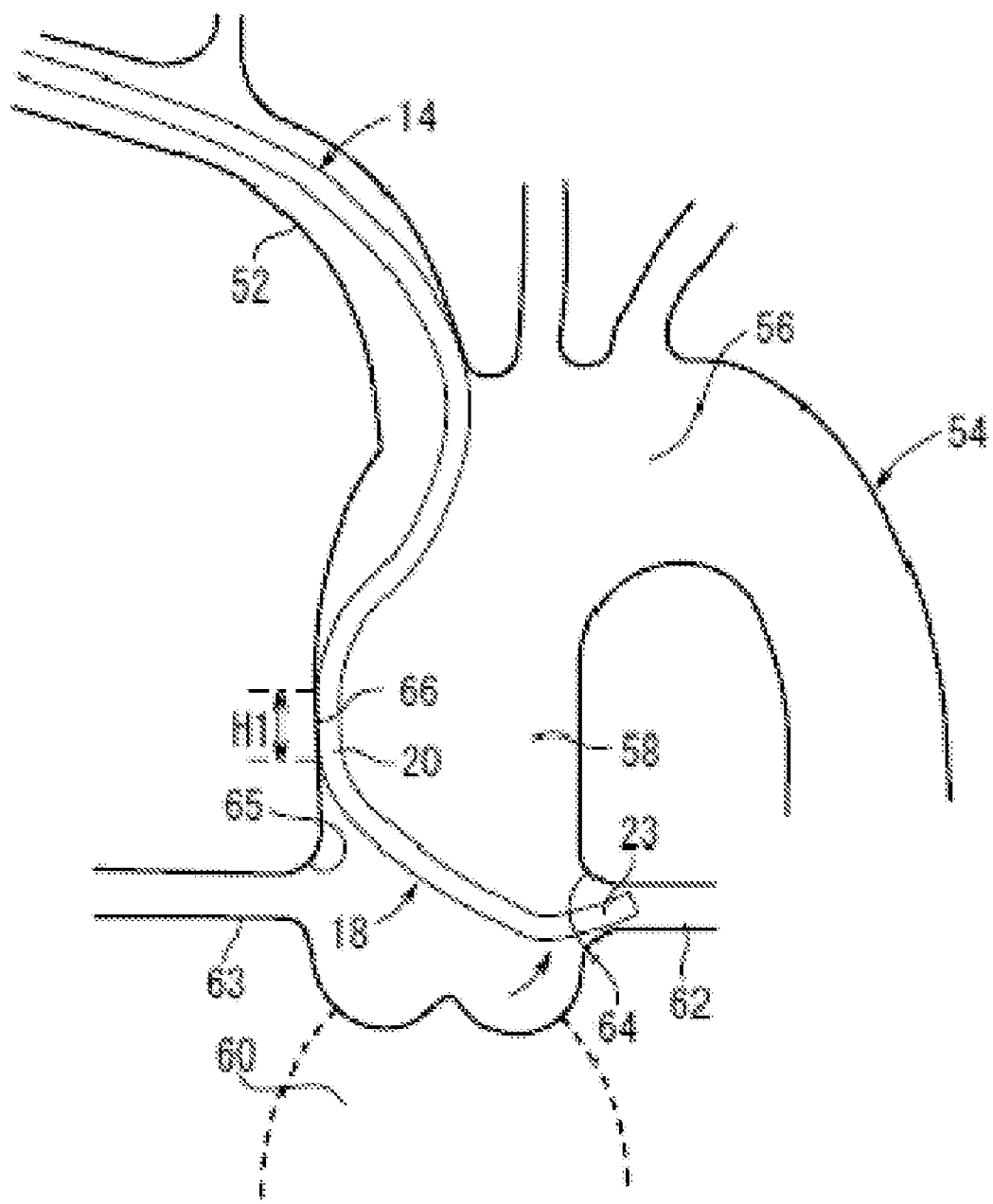
FIG. 6 is a similar view but showing the catheter for a coronary artery of FIG. 1 in another state wherein the distal end of the catheter for a coronary artery is engaged with the opening of the left coronary artery.

The curved portion 18 can be shaped such that, when the extreme distal end portion 23 is engaged with the left coronary artery opening 64, the axial line of the left coronary artery opening 64 and the axial line of the extreme distal end portion 23 are inclined relative to each other as seen in FIG. 6. Where the curved portion 18 is shaped in this manner, the extreme distal end portion 23 can be prevented from excessively advancing into the aorta and can be engaged at an appropriate position with the left coronary artery opening 64.

After the extreme distal end portion 23 is inserted into the left coronary artery opening 64 by the operation described above, the guide wire 48 is pulled out from the lumen 41 and a connector is connected to a Y connector 51 (refer to FIG. 4) mounted at a rear end of the hub 12 to inject contrast medium. The injected contrast medium passes through the lumen 41 and is jetted from the opening end of the lumen 41 into the left coronary artery 62, which is a target region. Consequently, confirmation of the inserted position of the catheter distal end in the left coronary artery opening 64 and imaging of the left coronary artery 62 are permitted. Then, a treatment catheter such as a PTCA balloon catheter (not shown) is inserted through a rear end portion of the Y connector 51 and the lumen 41.

In order to introduce the extreme distal end portion 23 of the catheter 10 into the right coronary artery opening 65, operation similar to that which is carried out when it is introduced into the left coronary artery opening 64 is carried out to introduce the catheter 10 into the aorta 54 as shown in FIG. 5. Thereupon, the catheter 10 is operated to rotate such that, when the guide wire 48 is pulled out from the curved portion 18, the direction to which the curved portion 18 is curved becomes the right coronary artery 63 side. Further, where the introduction target is changed over to the right coronary artery opening 65 in the state in which the extreme distal end portion 23 of the catheter 10 is introduced in the left coronary artery opening 64, the catheter 10 is returned to the state of FIG. 5 once and then the curved portion 18 is rotated by 180°.

Figure 7:
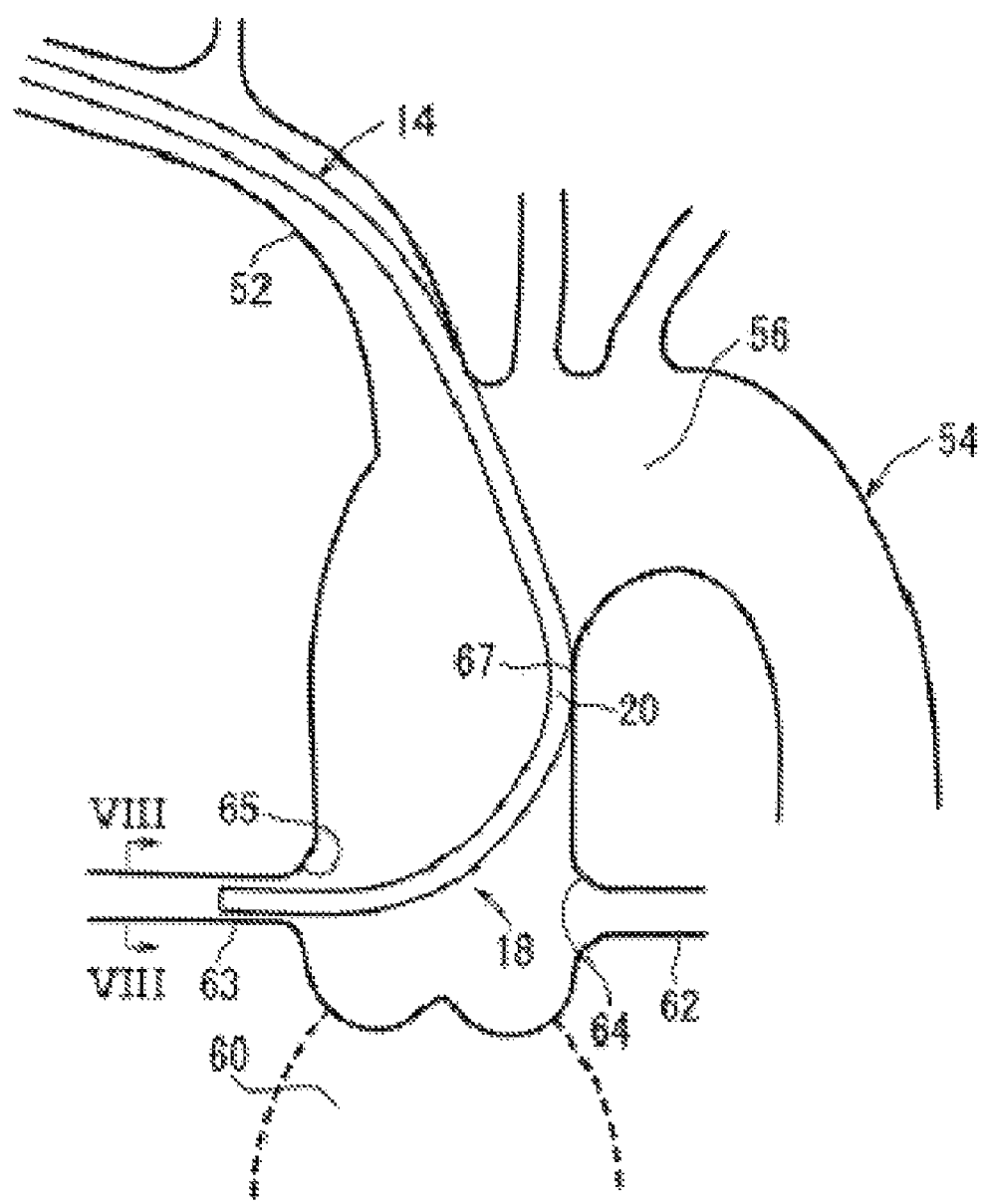
FIG. 7 is a similar view but showing the catheter for a coronary artery of FIG. 1 in a further state wherein the distal end of the catheter for a coronary artery is engaged with the opening of the right coronary artery.

Then, if the guide wire 48 is pulled out from the catheter main body 14, the curved portion 18 restores to its curved shape. By repulsive force generated by the shape restoration, the extreme distal end portion 23 is directed to the opening of the right coronary artery 63, that is, to the right coronary artery opening 65 and is inserted into the right coronary artery opening 65 as shown in FIG. 7. Consequently, the extreme distal end portion 23 is placed into a state in which it engages with the right coronary artery opening 65. It is to be noted that, if the extreme distal end portion 23 is not inserted in the right coronary artery opening 65, then if slight rotation is applied to the proximal end portion of the catheter 10 suitably, then the extreme distal end portion 23 is inserted readily into the right coronary artery opening 65.

In the state in which the extreme distal end portion 23 engages with the right coronary artery opening 65, the first curve 20 contacts with the aorta ascendens left wall 67 positioned on the opposite side to the right coronary artery opening 65, and backup support is carried out by the curved first curve 20.

As shown in FIG. 2, when the curved portion 18 is viewed from a particular point of view, the extreme distal end portion 23 of the curved portion 18 extends substantially linearly and obliquely to the interior side from the plane A in which the first curve 20, intermediate portion 21 and second curve 22 exist. Accordingly, the catheter 10 is shaped so that the extreme distal end portion 23 thereof can be introduced suitably into the right coronary artery opening 65. In particular, if the plane A in which the aorta 54 of a human being exists, that is, a plane in which the aorta ascendens 58 and the brachiocephalic artery 52 of a human being exist, is assumed and the aorta 54 and the right coronary artery 63 are viewed from the front side of the aorta 54, then the right coronary artery opening 65 is positioned in a slightly displaced relationship on the interior side with respect to the plane A in which the aorta 54 exists. Thus, with the catheter 10 of the present embodiment, since the extreme distal end portion 23 extends obliquely as described hereinabove with respect to the plane A in which the first curve 20, intermediate portion 21 and second curve 22 exist, when the curved portion 18 is inserted into the aorta 54, even if the first curve 20, intermediate portion 21 and second curve 22 are positioned in the plane in which the aorta 54 exists or a plane parallel to the plane, when the curved portion 18 restores its curved shape, the extreme distal end portion 23 is directed to the right coronary artery opening 65 side. Therefore, introduction of the extreme distal end portion 23 into the right coronary artery opening 65 can be carried out rapidly, reliably and easily.

Further, since the catheter 10 can be shaped such that it can be used for both of the left and right coronary artery openings 64 and 65, when the target of engagement of the catheter 10 is to be changed over from the left coronary artery opening 64 to the right coronary artery opening 65, if the curved portion 18 is rotated by 180°, then the extreme distal end portion 23 is directed to the right coronary artery opening 65. However, when the target of engagement is to be changed over from the right coronary artery opening 65 to the left coronary artery opening 64, if the curved portion 18 is rotated by 180°, then the extreme distal end portion 23 is directed to the left coronary artery opening 64. Accordingly, when the target of engagement is changed over between the left coronary artery opening 64 and the right coronary artery opening 65, the extreme distal end portion 23 can be engaged readily into the left or right coronary artery opening 64 or 65.

Figure 8:
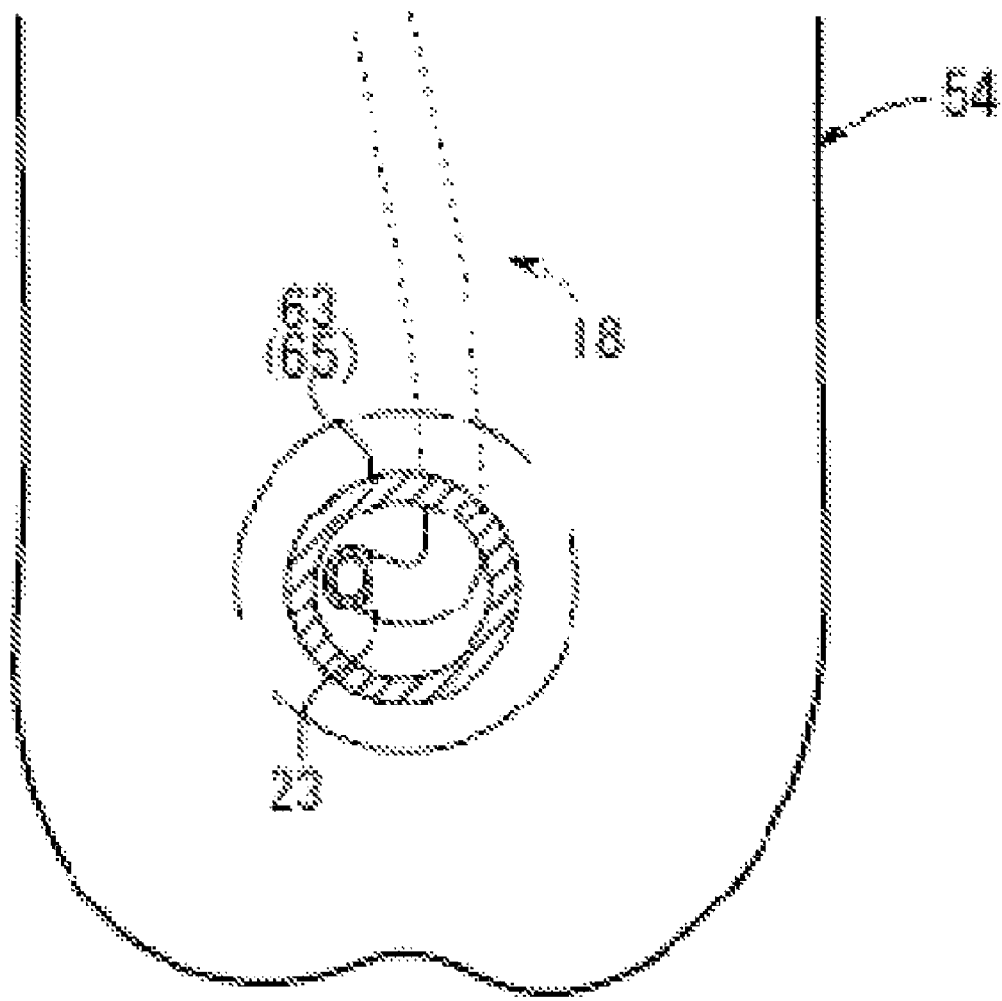
FIG. 8 is a sectional view taken along line VIII-VIII of FIG. 7.

FIG. 8 is a sectional view taken along line VIII-VIII of FIG. 7. The extreme distal end portion 23 can be inclined by an inclination angle α with respect to the plane A in which the first curve 20, intermediate portion 21 and second curve 22 exist as shown in FIG. 2. Therefore, when the extreme distal end portion 23 engages with the right coronary artery opening 65 as shown in FIG. 8, the axial line of the extreme distal end portion 23 is inclined with respect to the axial line of the right coronary artery opening 65. Consequently, the extreme distal end portion 23 can be prevented from excessively advancing into the interior of the right coronary artery 63, and can be engaged at an appropriate position with the right coronary artery opening 65.

Figure 9:
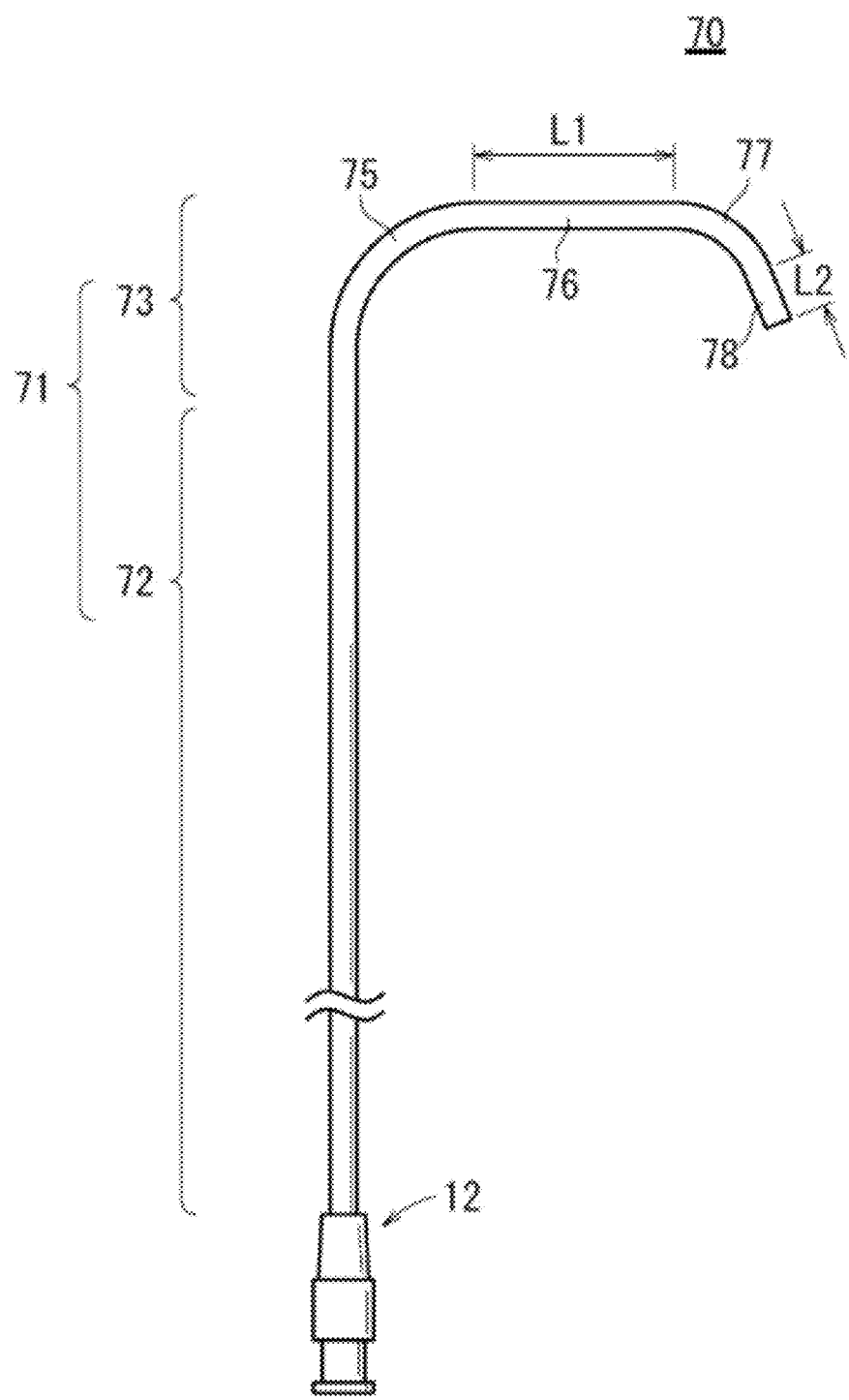
FIG. 9 is a partial plan view, showing a catheter for a coronary artery according to a comparative example.

FIG. 9 is a partial plan view, showing a catheter 70 for a coronary artery according to a comparative example. Referring to FIG. 9, the catheter 70 includes a catheter main body 71 having a main body portion 72 and a curved portion 73. The curved portion 73 includes a first curve 75, an intermediate portion 76, a second curve 77 and an extreme distal end portion 78. In the catheter 70 of the comparative example, the first curve 75, intermediate portion 76 and second curve 77 have a configuration similar to that of the first curve 20, intermediate portion 21 and second curve 22 of the catheter 10 of the embodiment of FIG. 1, respectively. However, the extreme distal end portion 78 exists on a plane same as that in which the first curve 75, intermediate portion 76 and second curve 77 exist.

Since the extreme distal end portion 78 of the catheter 70 of the comparative example configured as just described exists on the same plane as that in which the first curve 75, intermediate portion 76 and second curve 77 exist, when the curved portion 73 is introduced into the aorta 54, if the first curve 75, intermediate portion 76 and second curve 77 exist in the plane in which the aorta 54 exists or in a plane parallel to that plane. Then, when the curved portion 73 restores its curved shape, the extreme distal end portion 78 is directed to a position displaced a little from the left coronary artery opening 64 or the right coronary artery opening 65. Therefore, it may be necessary to operate the catheter 70 to carry out fine adjustment so that the extreme distal end portion 78 is directed to the left coronary artery opening 64 or the right coronary artery opening 65. In contrast, with the catheter 10 shown in FIG. 1, since the extreme distal end portion 23 can be directed to the left coronary artery opening 64 side or the right coronary artery opening 65 side when the curved portion 18 restores its curved shape, introduction of the catheter distal end into the left and right coronary artery openings 64 and 65 can be carried out rapidly, reliably and easily.

Figure 10:
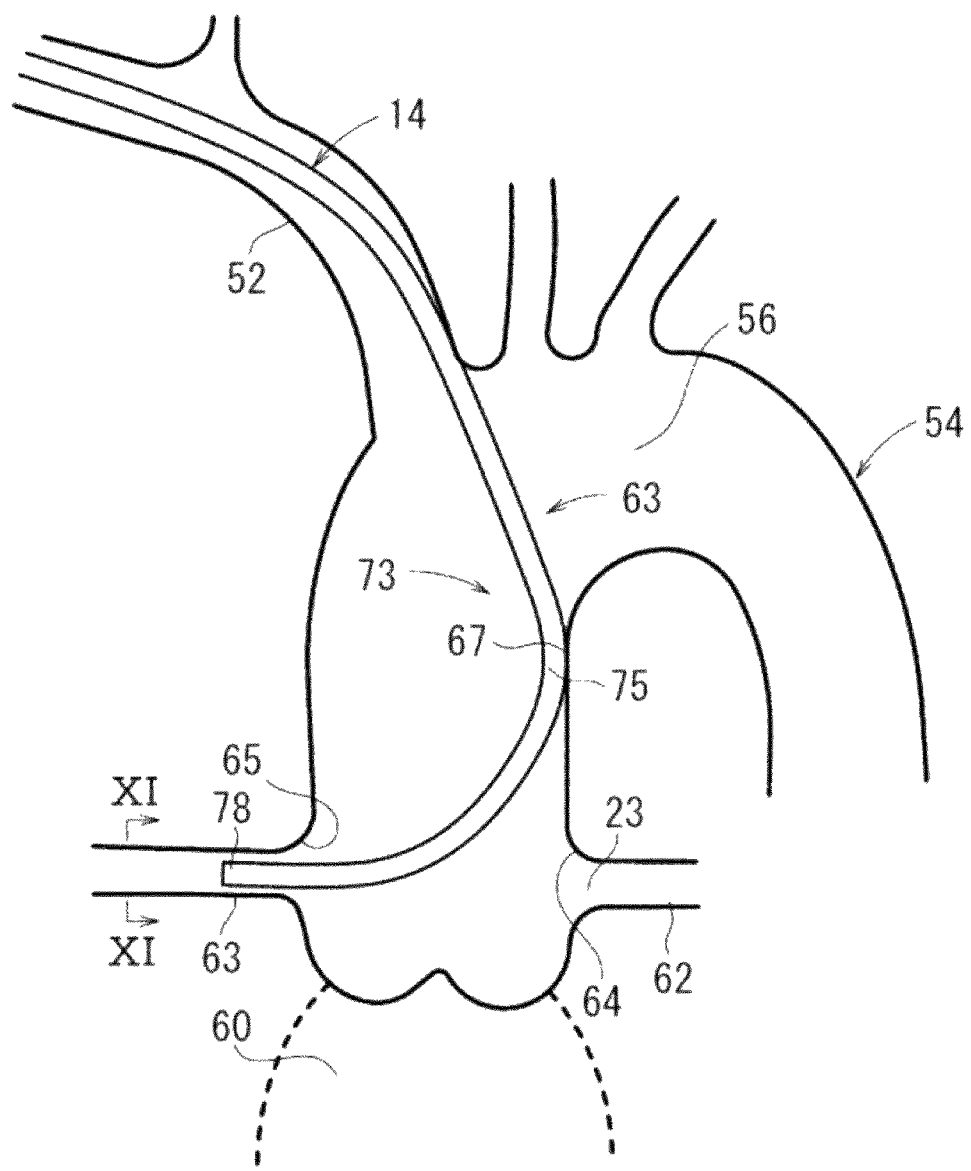
FIG. 10 is a schematic view showing the catheter for a coronary artery of FIG. 9 in a state wherein the distal end of the catheter for a coronary artery is engaged with the opening of the right coronary artery.
Figure 11:
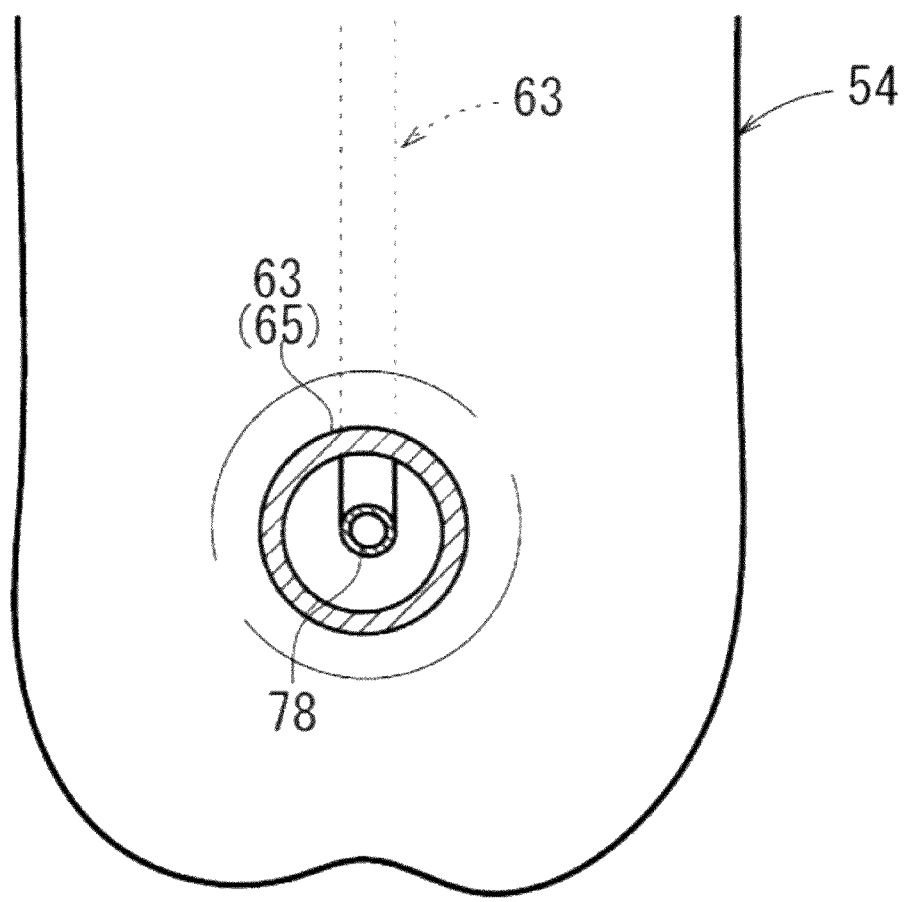
FIG. 11 is a sectional view taken along line XI-XI of FIG. 10.

FIG. 10 is a schematic view illustrating a state in which the extreme distal end portion 78 of the catheter 70 engages with the right coronary artery opening 65, and FIG. 11 is a sectional view taken along line XI-XI of FIG. 10. Since the extreme distal end portion 78 of the catheter 70 of the comparative example exists in the same plane as that in which the first curve 75, intermediate portion 76 and second curve 77 exist as described hereinabove, when the extreme distal end portion 78 is engaged with the right coronary artery opening 65, the axial line of the extreme distal end portion 78 extends substantially in parallel to the axial line of the right coronary artery opening 65 as seen in FIG. 11. In contrast, with the catheter 10 of the embodiment shown in FIG. 1, when the extreme distal end portion 23 is engaged with the right coronary artery opening 65, since the axial line of the extreme distal end portion 23 can be inclined with respect to the axial line of the right coronary artery opening 65 as described hereinabove, the extreme distal end portion 23 can be prevented from excessively advancing to the interior of the right coronary artery 63, and can be engaged at an appropriate position with the right coronary artery opening 65.

Figure 12:
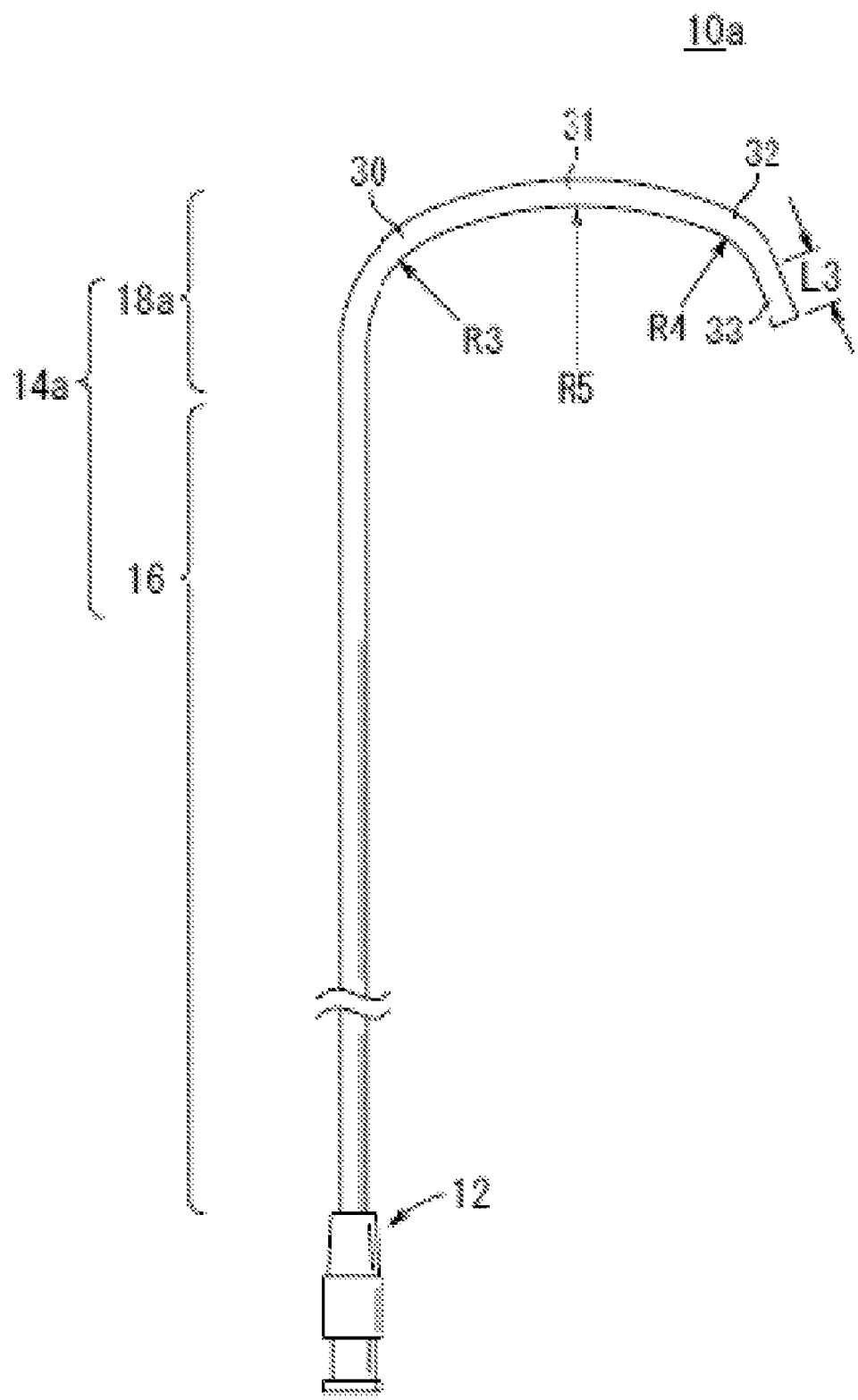
FIG. 12 is a partial plan view, showing a catheter for a coronary artery according to another embodiment of the disclosed subject matter.

FIG. 12 is a partial plan view, showing a catheter 10a for a coronary artery according to another embodiment of the disclosed subject matter. It is to be noted that, in the catheter 10a, those elements having similar functions or effects to those described with respect to the catheter 10 according to the embodiment of FIG. 1 are denoted by like reference characters and overlapping description of these elements omitted herein to avoid redundancy.

Referring to FIG. 12, the catheter 10a can include a catheter main body 14a having flexibility and having a hollow structure, and a hub 12 formed at a proximal end portion of the catheter main body 14a. The outer diameter of the catheter main body 14a can be equal to or smaller than 2.7 mm, and possibly equal to or smaller than 2.1 mm over an overall length thereof similarly to the catheter main body 14 described hereinabove with reference to FIG. 1.

The catheter main body 14a can have a lumen at a substantially central portion thereof and a structure wherein an inner layer, an intermediate layer and an outer layer are laminated in that order from the inner side to the outer side similar to the structure of the catheter main body 14 described hereinabove with reference to FIG. 3. A metal mesh can be embedded in the intermediate layer.

The catheter main body 14a can have a main body portion 16 that has a substantially linear shape in a natural state, and a curved portion 18a configuring a portion extending from the main body portion 16 to the distal end and having a curved shape in a natural state. The curved portion 18a can be configured from a first curve 30 extending in a curved shape from the main body portion 16, an intermediate portion 31 extending from the first curve 30, a second curve 32 extending from the intermediate portion 31 and curved in a direction that is the same as that of the first curve 30, and a substantially linear extreme distal end portion 33 extending from the second curve 32. The first curve 30, intermediate portion 31 and second curve 32 can exist on a substantially same plane.

The first curve 30 can exhibit a curved shape in a natural state thereof, that is, can exhibit a shape curved in the clockwise direction from the main body portion 16 in FIG. 12. Exemplary ranges of the radius R3 of curvature of the first curve 30 and the angle of the first curve 30, that is, the range over which the first curve 30 extends around the center of curvature, are similar to those of the first curve 20 in the embodiment of FIG. 1. In the configuration example shown in FIG. 12, the radius R3 of curvature of the first curve 30 is set to 15 mm and the angle of the first curve 30 is set to 70°.

The intermediate portion 31 can exhibit a curved shape, that is, a shape curved in the clockwise direction from the first curve 30 in FIG. 12, in a natural state thereof. The radius R3 of curvature, the angle and the length of an arc of the intermediate portion 31 can be set such that, when the extreme distal end portion 33 engages with the left coronary artery opening 64, the first curve 30 contacts with the aorta inner wall on the opposite side to the left coronary artery opening 64, that is, with the aorta ascendens right wall 66, and, when the extreme distal end portion 33 engages with the right coronary artery opening 65, the first curve 30 contacts with the aorta inner wall on the opposite side to the right coronary artery opening 65, that is, with the aorta ascendens left wall 67. Consequently, the first curve 30 can contact with certainty with the aorta inner wall and the extreme distal end portion 33 can be prevented from being disengaged from the left coronary artery opening 64 or the right coronary artery opening 65. From such a point of view as just described, the radius R5 of curvature, the angle, and the length of the arc of the intermediate portion 31 can be set to approximately 25 to 70 mm, 30 to 70°, and 10 to 40 mm, respectively. In the configuration example shown in FIG. 12, the intermediate portion 31 is set such that the radius R5 of curvature is 35 mm, the angle is 55° and the length of the arc is 20 mm.

The second curve 32 can exhibit a curved shape, that is, a shape curved in the clockwise direction from the intermediate portion 31 in FIG. 12, in a natural state thereof. Ranges of the radius of curvature and the angle of the second curve 32 can be similar to those of the first curve 20 in the first embodiment. In the configuration example shown in FIG. 12, the radius R4 of curvature of the second curve 32 is set to 8 mm and the angle of the second curve 32 is set to 60°.

The extreme distal end portion 33 can have a substantially linear shape in a natural state thereof. The length L3 of the extreme distal end portion 33 can be set to such a degree that the extreme distal end portion 33 can be inserted into and self-retained in the left coronary artery opening 64 and the right coronary artery opening 65 without excessively entering them, and can be set particularly to approximately 5 to 50 mm. In the configuration example shown in FIG. 12, the length L3 of the extreme distal end portion 33 is set to 7 mm. The curved portion 18a can be shaped such that, when the extreme distal end portion 33 is positioned in the left coronary artery opening 64, it is inclined with respect to the axial line direction of the left coronary artery opening 64.

The curved portion 18a can be configured from only four components of the first curve 30, intermediate portion 31, second curve 32 and extreme distal end portion 33. Where the curved portion 18a is configured in this manner, and when the catheter 10a is circulated in a blood vessel, the resistance in the blood vessel can be lower than that of a catheter which has a greater number of curves and the passing property of a device for treatment in the catheter 10a is good. Further, it is easy to apply torque to the catheter 10a.

With the catheter 10a shaped in such a manner as described above, the extreme distal end portion 33 can be engaged selectively with any of the left coronary artery opening 64 and the right coronary artery opening 65.

Figure 13:
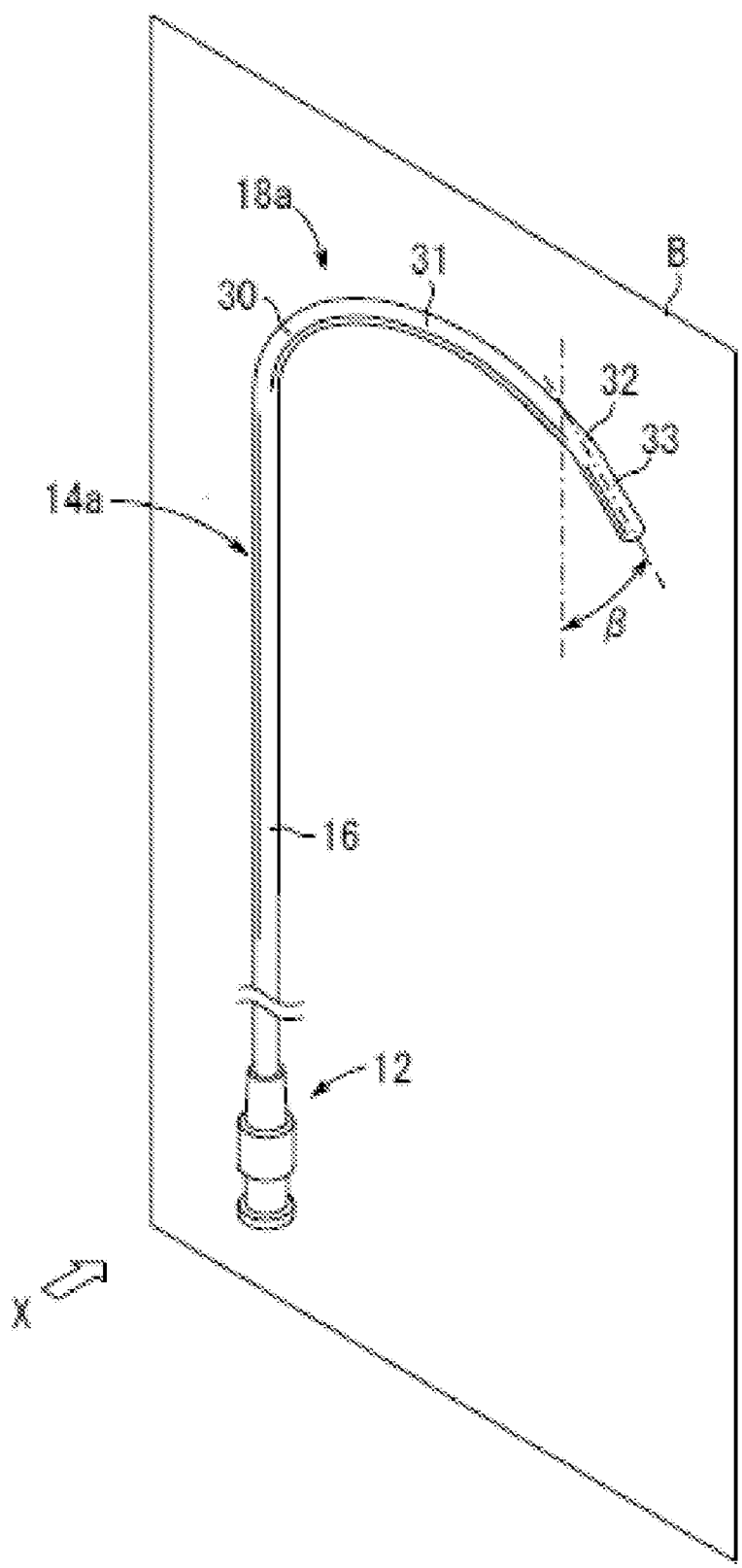
FIG. 13 is a partial perspective view, showing a three-dimensional shape of the catheter for a coronary artery of FIG. 12.

FIG. 13 is a partial perspective view, showing a three-dimensional shape of the catheter 10a. Referring to FIG. 13, a plane B in which the first curve 30, intermediate portion 31 and second curve 32 exist is assumed. Further, if it is assumed that the curved portion 18a is positioned on the upper side of the main body portion 16 and is viewed from a point of view at which the curved portion 18a is positioned on the right side of the main body portion 16, that is, from a point of view in the direction indicated by arrow X in FIG. 13, then the extreme distal end portion 33 extends substantially linearly and at an oblique angle to the interior side (back side) from plane B. In other words, the extreme distal end portion 33 can extend substantially linearly and obliquely away from a point of a viewer when the catheter 10a is viewed from a point of view at which the curved portion is positioned on a right side and at a top of the main body portion (i.e., the extreme distal end portion 33 can extend into the paper as viewed in FIG. 13). The inclination angle β of the extreme distal end portion 33 with respect to the plane B can be set to 10 to 30°, and possibly approximately 16 to 20°. In the configuration example shown in FIG. 2, the inclination angle β is set to 18°.

The catheter 10a according to the embodiment of FIG. 12 is basically configured in such a manner as described above, and operation and effects of the catheter 10a are described below. The following description is directed to an example of a method of use of the catheter 10a wherein the catheter 10a is used as a guiding catheter which is used together with a treatment catheter.

Figure 14:
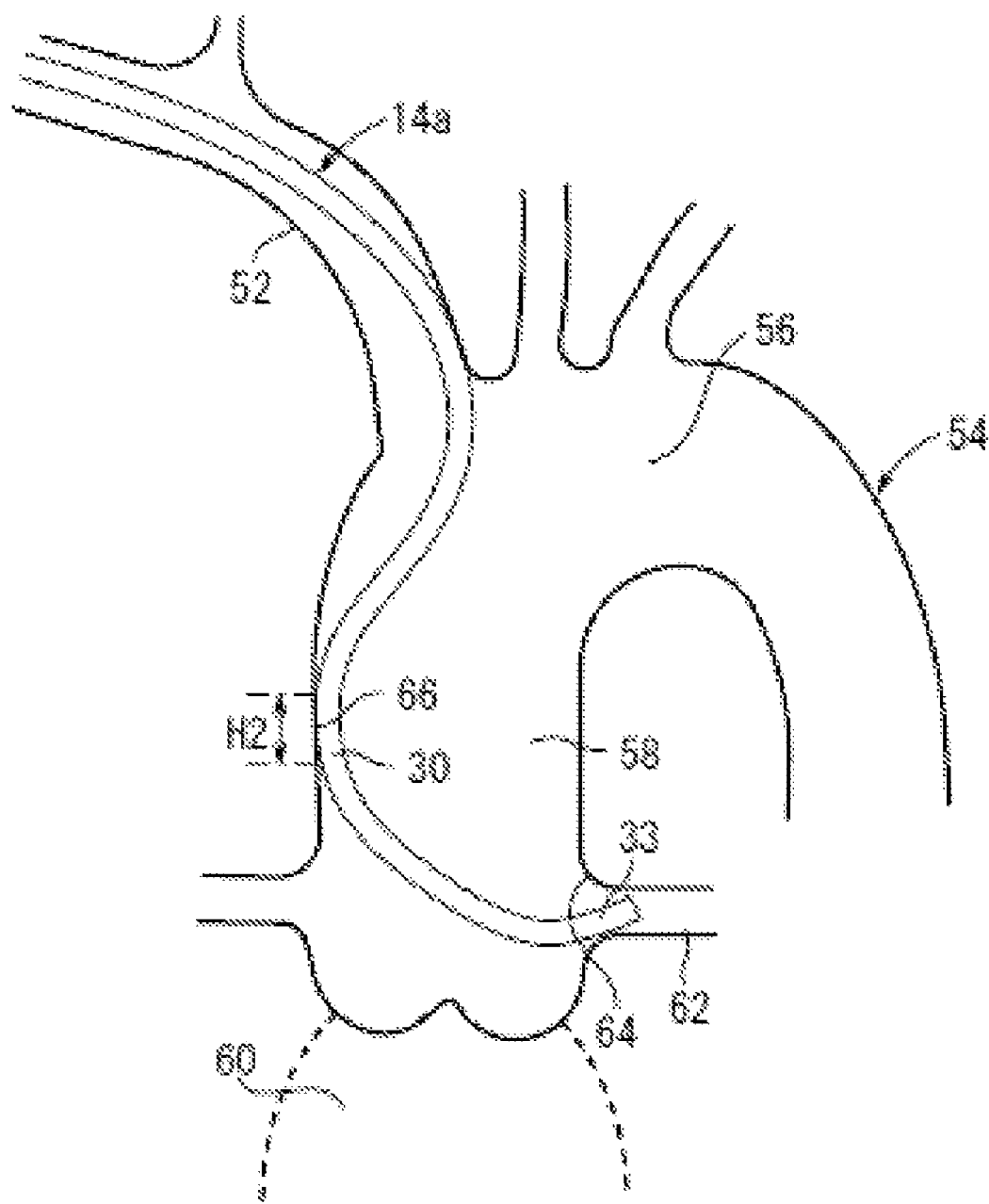
FIG. 14 is a schematic view showing the catheter for a coronary artery of FIG. 12 in a state wherein the distal end of the catheter is engaged with the opening of the left coronary artery.

FIG. 14 is a schematic view illustrating a state in which the extreme distal end portion 33 of the catheter of the embodiment of FIG. 12 engages with the left coronary artery opening 64. Operation of the catheter 10a when the extreme distal end portion 33 is engaged with the left coronary artery opening 64 can be similar to that of the catheter 10 according to the embodiment of FIG. 1.

As described above, with the catheter 10a, the extreme distal end portion 33 can be configured to extend obliquely with respect to the plane B in which the first curve 30, intermediate portion 31 and second curve 32 exist. Accordingly, similarly as in the case of the catheter 10 according to the embodiment of FIG. 1, when the curved portion 18a is introduced into the aorta 54, even if the first curve 30, intermediate portion 31 and second curve 32 are positioned in the plane in which the aorta 54 exists or in a plane parallel to this plane, the extreme distal end portion 33 is directed to the left coronary artery opening 64 side. Therefore, introduction of the extreme distal end portion 33 into the left coronary artery opening 64 can be carried out rapidly, reliably and easily.

In the catheter according to the embodiment of FIG. 12, the first curve 30 can be shaped such that the contact length H2 thereof with the aorta inner wall, that is, the aorta ascendens right wall 66 in FIG. 14, is less than 10 mm. If the contact length H2 between the first curve 30 and the aorta inner wall is less than 10 mm, then the direction of the curved portion 18a can be changed readily around a fulcrum provided by the first curve 30. Accordingly, the direction of the catheter distal end, that is, the extreme distal end portion 33, can be changed readily.

The curved portion 18a can be shaped such that, when the extreme distal end portion 33 is engaged with the left coronary artery opening 64, the axial line of the left coronary artery opening 64 and the axial line of the extreme distal end portion 33 are inclined relative to each other as shown in FIG. 14. Where the curved portion 18a is shaped in this manner, the extreme distal end portion 33 can be prevented from excessively advancing to the interior side of the left coronary artery 62 and can be engaged at an appropriate position with the left coronary artery opening 64.

Figure 15:
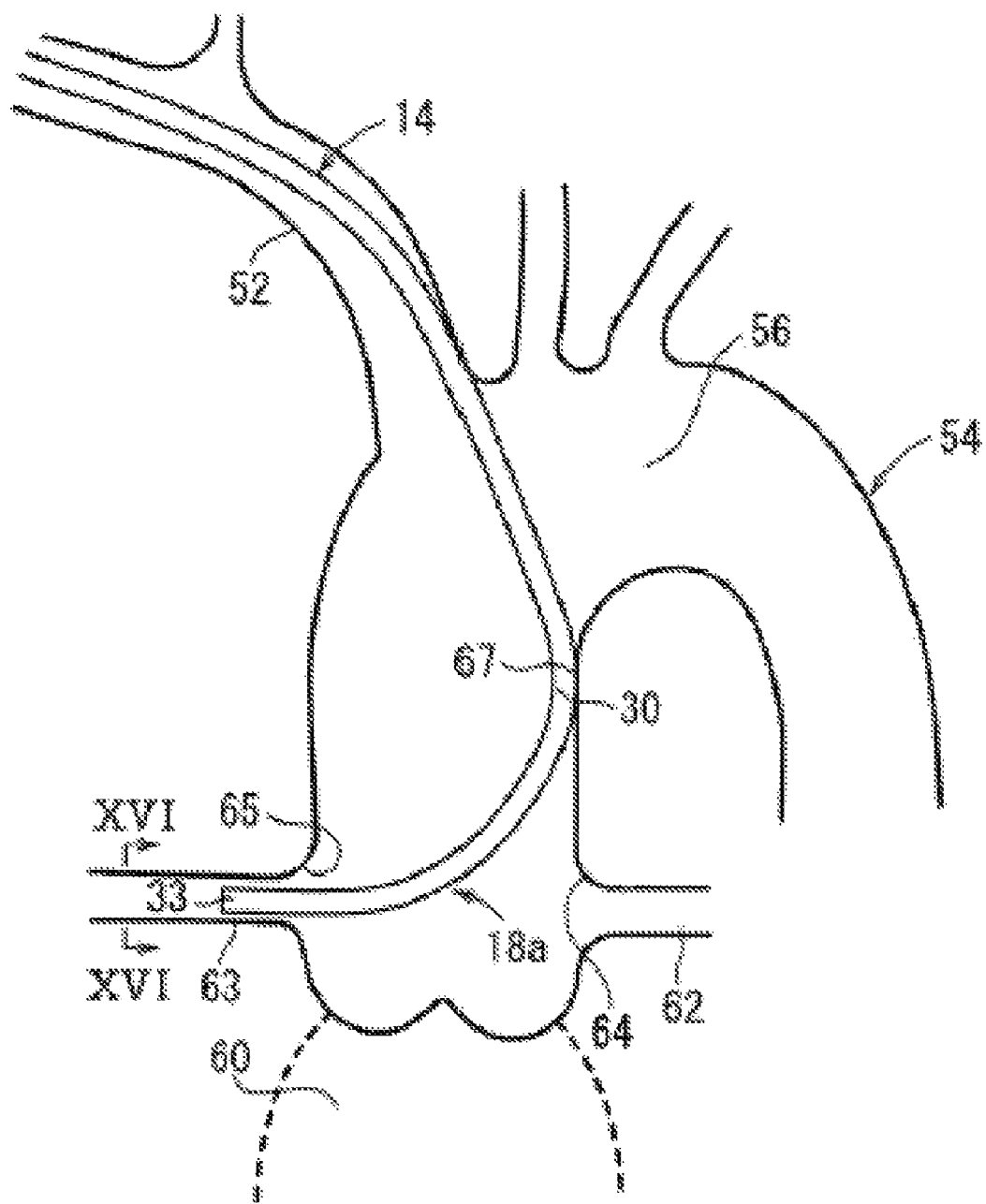
FIG. 15 is a similar view but showing the catheter for a coronary artery of FIG. 12 in another state wherein the distal end of the catheter is engaged with the opening of the right coronary artery.

FIG. 15 is a schematic view illustrating a state in which the extreme distal end portion 33 of the catheter 10a according to the embodiment of FIG. 12 engages with the right coronary artery opening 65. Operation of the catheter 10a when the extreme distal end portion 33 is engaged with the right coronary artery opening 65 can be similar to that of the catheter 10 according to the embodiment of FIG. 1. Referring to FIG. 15, in a state in which the extreme distal end portion 33 engages with the right coronary artery opening 65, the first curve 30 contacts with the aorta ascendens left wall 67 positioned on the opposite side to the right coronary artery opening 65, and backup support is carried out by the first curve 30.

As described hereinabove, in the catheter 10a, the extreme distal end portion 33 can extend obliquely with respect to the plane B in which the first curve 30, intermediate portion 31 and second curve 32 exist. Accordingly, similar to the catheter 10 according to the embodiment of FIG. 1, when the curved portion 18a is introduced into the aorta 54, even if the first curve 30, intermediate portion 31 and second curve 32 exist in the plane in which the aorta 54 exists or in a plane parallel to this plane, when the curved portion 18a restores its curved shape, the extreme distal end portion 33 can be directed to the right coronary artery opening 65 side. Therefore, introduction of the extreme distal end portion 33 into the right coronary artery opening 65 can be carried out rapidly, reliably and easily.

Figure 16:
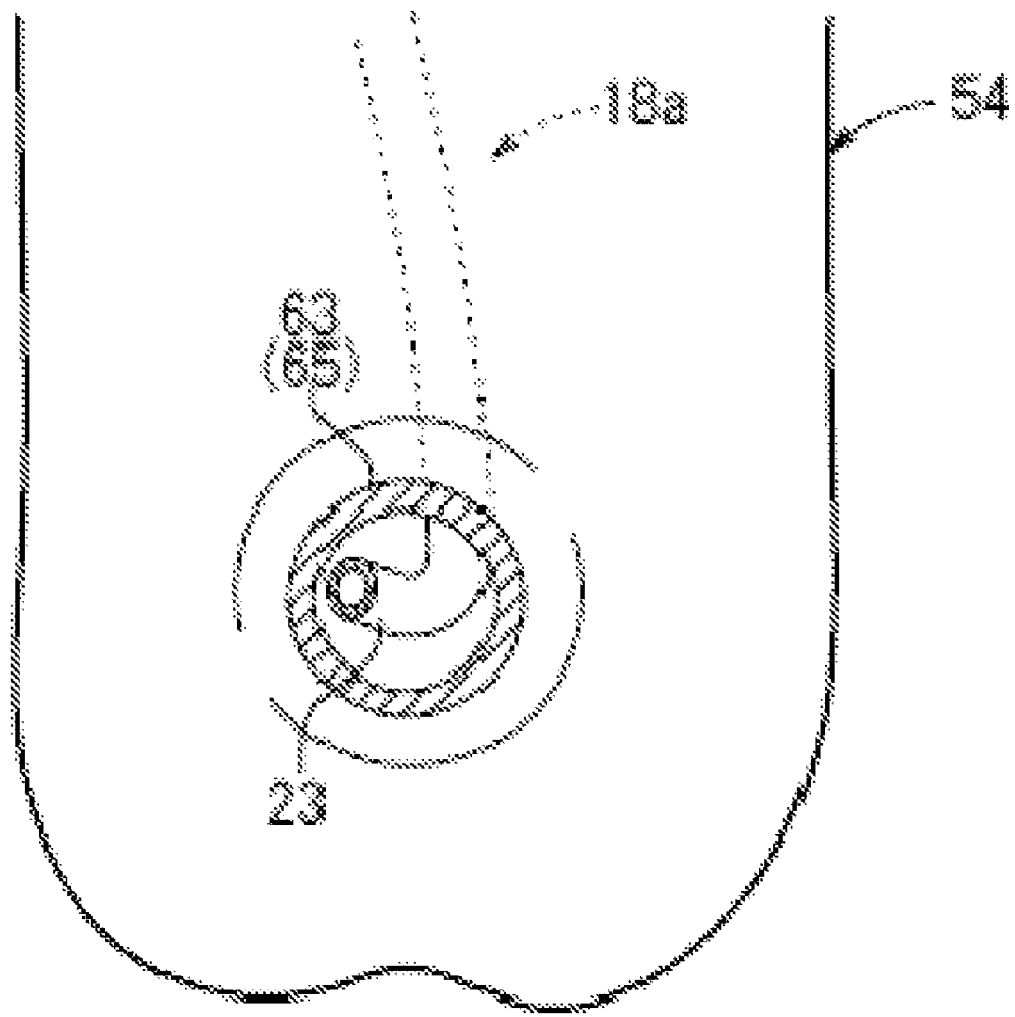
FIG. 16 is a sectional view taken along line XVI-XVI of FIG. 15.

FIG. 16 is a sectional view taken along line XVI-XVI of FIG. 15. As shown in FIG. 13, the extreme distal end portion 33 is inclined by the inclination angle β with respect to the plane B in which the first curve 30, intermediate portion 31 and second curve 32 exist. Therefore, when the extreme distal end portion 33 engages with the right coronary artery opening 65, the longitudinal axial line of the extreme distal end portion 33 is inclined with reference to the longitudinal axial line of the right coronary artery opening 65 as shown in FIG. 16. Consequently, the extreme distal end portion 33 can be prevented from excessively advancing to the interior side of the right coronary artery and can be engaged at an appropriate position with the right coronary artery opening 65.

It is to be noted that it is a matter of course that, in the embodiment of FIG. 13, the components common to those of the embodiment of FIG. 1 can achieve the same or similar operational characteristics and effects to those achieved by the common components in the embodiment of FIG. 1.

Method of Use of Catheter of FIG. 1

As regards a method of use of the catheter 10 according to the embodiment of FIG. 1, the following description is given. In particular, after the extreme distal end portion 23 of the catheter 10 is engaged with the left coronary artery opening 64, it is moved back to the neighborhood of the center of the aorta ascendens 58 once and then is rotated to change over the target of engagement to the right coronary artery opening 65. However, engagement of the extreme distal end portion 23 of the catheter 10 may otherwise be carried out in the following manner.

As shown in FIG. 5, the catheter 10 introduced into the aorta ascendens 58 from the brachiocephalic artery 52 advances in the blood vessel while rotating a little until the extreme distal end portion 23 reaches the aorta ascendens 58. From the relationship between the curve of a portion of the brachiocephalic artery 52 proximate to the aorta and the shape of the curved portion 18 of the catheter 10, when the catheter distal end, that is, the extreme distal end portion 23, reaches the aorta ascendens 58, the catheter distal end is liable to be automatically directed to the right coronary artery opening 65. If the catheter distal end is positioned near to the right coronary artery opening 65, the catheter 10 can be operated at the proximal end portion thereof to rotate to engage the extreme distal end portion 23 with the right coronary artery opening 65. After the extreme distal end portion 23 of the catheter 10 is engaged with the right coronary artery opening 65, a desired process such as, for example, injection of contrast medium or insertion of a treatment catheter can be carried out.

Then, the extreme distal end portion 23 can be removed from the right coronary artery opening 65, that is, the engagement of the extreme distal end portion 23 is canceled. In this instance, the extreme distal end portion 23 is not returned to a position in the proximity of the center of the aorta ascendens 58, but is left staying in the proximity of the right coronary artery opening 65. When the extreme distal end portion 23 is disengaged from the right coronary artery opening 65, the proximal end portion of the catheter 10 can be rotated in the counterclockwise direction in this manner, then the shaft of the catheter 10 rotates in the counterclockwise direction. This rotation is taken from a point of view at which the aorta valve side is viewed from the aorta ascendens 58 side, around the center line or lengthwise/longitudinal axis of the aorta 54 in the inside of the aorta 54, particularly in the inside of the aorta ascendens 58 and the aortic arch 56.

Figure 17A:
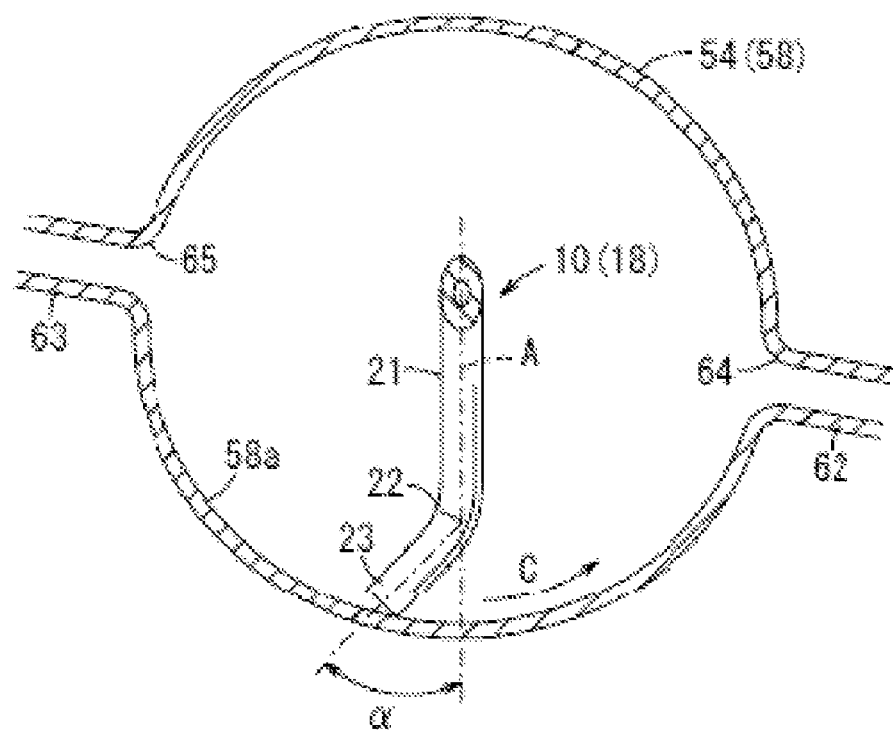
FIG. 17A is a schematic view illustrating a behavior of the extreme distal end of the catheter for a coronary artery of FIG. 1 when the engaging target of the extreme distal end is changed over from the opening of the right coronary artery to the opening of the left coronary artery.

FIG. 17A illustrates a behavior of the extreme distal end portion 23 in this instance and shows a cross section perpendicular to the axial line of the aorta ascendens 58 including the left and right coronary artery openings 64 and 65. In particular, the extreme distal end portion 23 rotates so as to pass the front side of the body of a patient from a position in the proximity of the right coronary artery opening 65 while contacting with the aorta wall 58a of the aorta 54 until it comes to the neighborhood of the left coronary artery opening 64. Then, the extreme distal end portion 23 is further rotated until it is engaged with the left coronary artery opening 64.

Figure 17B:
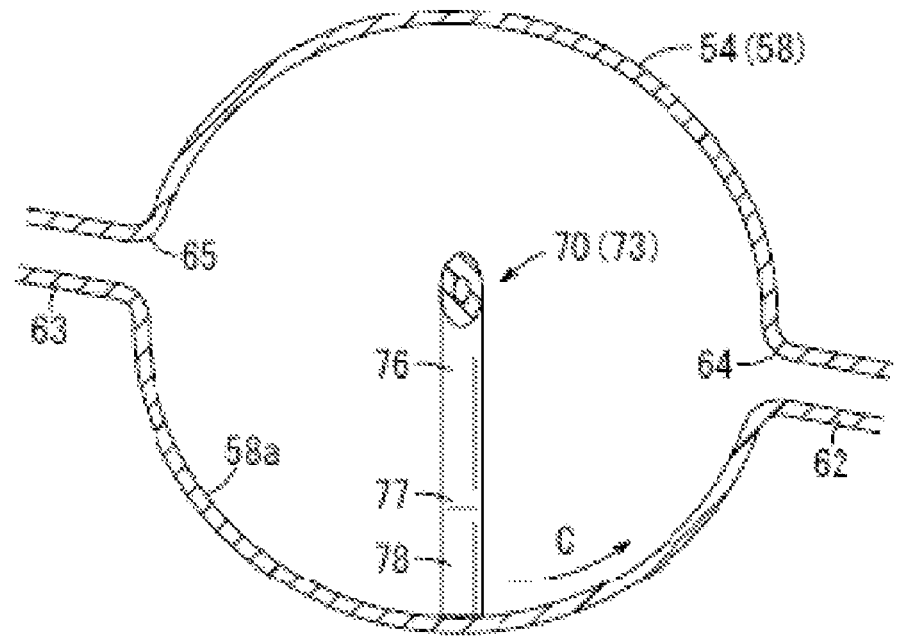
FIG. 17B is a schematic view illustrating a behavior of the extreme distal end of the catheter for a coronary artery of FIG. 9 when the engaging target of the extreme distal end is changed over from the opening of the right coronary artery to the opening of the left coronary artery.

Incidentally, if the extreme distal end portion 78 is rotated along the aorta wall 58a in a similar manner as described above by manual operation using the catheter 70 (refer to FIG. 9) configured such that the extreme distal end portion 78 exists in a plane that is the same as the plane in which the first curve 75, intermediate portion 76 and second curve 77 exist, then the extreme distal end portion 78 rotates along the aorta wall 58a in contact substantially right-angularly to the aorta wall 58a, as shown in FIG. 17B. Therefore, there is the possibility that the extreme distal end portion 78 may damage the aorta wall 58a.

In contrast, with the catheter 10, the extreme distal end portion 23 is inclined with respect to the plane A in which the first curve 20, intermediate portion 21 and second curve 22 exist, as seen in FIG. 2. Therefore, when the extreme distal end portion 23 is rotated in such a manner as described above along the aorta wall 58a, the extreme distal end portion 23 smoothly moves along the aorta wall 58a while contacting at an outer circumferential face thereof with the aorta wall 58a in such a state that it forms an angle less than a right angle with respect to the aorta wall 58a, as shown in FIG. 17A. Therefore, the extreme distal end portion 23 is less likely to damage the aorta wall 58a.

It is to be noted that engagement of the extreme distal end portion 23 with the left and right coronary artery openings 64 and 65 may be carried out in an order of the left coronary artery opening 64 and the right coronary artery opening 65 opposite to that described hereinabove. In particular, the extreme distal end portion 23 can be engaged with the left coronary artery opening 64 first, and then the extreme distal end portion 23 is disengaged from the left coronary artery opening 64 and the proximal end portion of the catheter 10 is rotated in the counterclockwise direction. Consequently, the extreme distal end portion 23 rotates in the counterclockwise direction at a point of view at which the aorta valve side is viewed from the aorta ascendens 58 side. In this instance, the extreme distal end portion 23 rotates passing the rear side of the body of the patient from a location in the proximity of the left coronary artery opening 64 while contacting with the aorta wall 58a until it comes to the neighborhood of the right coronary artery opening 65. Then, the extreme distal end portion 23 is further rotated until it is engaged with the right coronary artery opening 65. In this instance, the extreme distal end portion 23 smoothly moves in a state in which it forms an angle less than a right angle with respect to the aorta wall 58a while an outer circumferential face thereof contacts with the aorta wall 58a. Therefore, the extreme distal end portion 23 is less likely to damage the aorta wall 58a.

If it is intended to achieve smoother movement of the extreme distal end portion 23 when the target of engagement is changed over from the right coronary artery opening 65 to the left coronary artery opening 64, then the extreme distal end portion 23 which has engaged with the right coronary artery opening 65 may be pulled back to the proximal end side until the state of FIG. 5 is reached thereby to move the extreme distal end portion 23 away from the aorta wall 58a, whereafter the extreme distal end portion 23 is rotated so as to be directed to the left coronary artery opening 64. In this instance, when the guide wire is pulled out from the catheter main body 14 to allow the curved portion 18 to restore its original curved shape, the extreme distal end portion 23 is not engaged directly with the left coronary artery opening 64 but is contacted principally with a region of the patient displaced forwardly. In order to cause the extreme distal end portion 23 to be engaged with the left coronary artery opening 64, the proximal end portion of the catheter 10 is rotated in the counterclockwise direction to move the extreme distal end portion 23 to the left coronary artery opening 64. In this instance, the extreme distal end portion 23 smoothly moves along the aorta wall 58a in a state in which it forms an angle less than a right angle with respect to the aorta wall 58a while an outer circumferential face thereof contacts with the aorta wall 58a. Therefore, the extreme distal end portion 23 is less likely to damage to the aorta wall 58a.

In order to provide smoother movement of the extreme distal end portion 23 when the target of engagement is changed over from the left coronary artery opening 64 to the right coronary artery opening 65, the extreme distal end portion 23 which has engaged with the left coronary artery opening 64 can be pulled back to the proximal end side until the state of FIG. 5 is established thereby to move the extreme distal end portion 23 far away from the aorta wall 58a. Then, the extreme distal end portion 23 can be rotated so as to be directed to the right coronary artery opening 65, and then the extreme distal end portion 23 can be contacted with a location of the patient displaced to the rear side with respect to the right coronary artery opening 65 and moved to the right coronary artery opening 65. Also in this instance, the extreme distal end portion 23 smoothly moves in a state in which it forms an angle less than a right angle with respect to the aorta wall 58a while an outer circumferential face thereof contacts with the aorta wall 58a.

As apparent from the foregoing description, the catheter 10 can be configured such that the extreme distal end portion 23 is engaged with one of the left coronary artery opening 64 and the right coronary artery opening 65, such that the extreme distal end portion 23 is disengaged from one of the left coronary artery opening 64 and the right coronary artery opening 65, such that the extreme distal end portion 23 is rotated along the aorta wall 58a in a direction in which the angle formed by the extreme distal end portion 23 with respect to the aorta wall 58a decreases, and such that the extreme distal end portion 23 is engaged with the other of the left coronary artery opening 64 and the right coronary artery opening 65.

In order to confirm the operational characteristics and effects of the catheter 10 wherein the intermediate portion 21 is formed in a linear fashion, a use test was carried out for working examples 1-1 to 1-5 among which the angle α is different and a catheter wherein the inclination angle α is 0, that is, the catheter 70 shown in FIG. 10 (hereinafter referred to as comparative example). In this test, the catheters 10 and 70 according to the working example and the comparative example 1, respectively, were inserted into a transparent model of the aorta and the coronary artery of the size of the original in water of 37° C. Then, the extreme distal end portion 23 was engaged with the right coronary artery opening. Thereafter, the extreme distal end portion 23 was disengaged from the right coronary artery opening and rotated in a direction corresponding to the direction indicated by an arrow mark C in FIG. 17A until it was engaged with the left coronary artery opening. Results are indicated in Table 1 below.

TABLE 1

| | α | α' | α'' | Inside the aorta | The degree of lesion inside the blood vessel — Inside the coronary artery |
|---|---|---|---|---|---|
| Comparative Example 1 | 0 | 0 | 0 | serious | moderate |
| Example 1-1 | 8 | 12 | 2 | moderate | moderate |
| Example 1-2 | 10 | 15 | 5 | slight | slight |
| Example 1-3 | 16 | 25 | 8 | slight | slight |
| Example 1-4 | 30 | 40 | 15 | slight | slight |
| Example 1-5 | 35 | 50 | 20 | slight | moderate |

In Table 1, the angle α is an angle at which the extreme distal end portion 23 projects obliquely three-dimensionally with respect to the plane A, which is a reference plane, shown in FIG. 2 in a natural state, that is, in a state in which no external force acts. The angle α' is an inclination angle of the extreme distal end portion 23 with respect to the plane A when the extreme distal end portion 23 moves along the aorta wall (refer to FIG. 17A). The angle α'' is an angle at which a longitudinal axis of the extreme distal end portion 23 is inclined with respect to a longitudinal axial line of the coronary artery when the extreme distal end portion 23 is engaged with the coronary artery opening.

Further, in Table 1, the words "slight," "moderate," and "serious" indicate different degrees of influence on the aorta or the coronary artery, and the round mark represents the possibility that a blood vessel wall may be damaged is very low; the triangular mark represents that the possibility that a blood vessel wall may be damaged is low; and the cross mark represents that there is the possibility that a blood vessel wall may be damaged.

While the working examples 1-1 to 1-5 are involved as seen in Table 1, details of the working example 1-2, in which the angle α is 10°, is described as a representative of the examples. The other working examples are described only in outline.

The catheter 10 according to the working example 1-2 was inserted into the model described hereinabove and the extreme distal end portion 23 was engaged with the right coronary artery opening. In this instance, as described hereinabove with reference to FIG. 8, the extreme distal end portion 23 extended not coaxially with the right coronary artery opening but slightly obliquely. Therefore, the extreme distal end portion 23 was engaged with the right coronary artery opening in a state in which the outer circumferential face thereof contacted with a side face of the inner wall of the right coronary artery opening. In this state, a balloon catheter having a guide wire placed therein was inserted into the right coronary artery. In this instance, the user was able to operate the balloon catheter readily without a feel of an obstacle.

Then, the extreme distal end portion 23 was disengaged from the right coronary artery opening, and the proximal end portion of the catheter 10 was rotated in the counterclockwise direction. Although the extreme distal end portion 23 of the catheter 10 was deformed at this time, an angle less than a right angle with respect to the aorta wall was formed so that the extreme distal end portion 23 was rotated smoothly while contacting with the aorta wall without a feel of an obstacle at the extreme distal end portion 23. The catheter 10 was further operated so that the extreme distal end portion 23 was engaged with the left coronary artery opening 64 in a non-coaxial state, that is, in a state in which the longitudinal axis of the extreme distal end portion 23 was inclined with respect to a longitudinal axial line of the left coronary artery 62 extending from the left coronary artery opening 64. In this state, the balloon catheter with a guide wire was inserted into the left coronary artery. In this instance, the user was able to operate the balloon catheter without the feel of an obstacle.

As regards the working example 1-1, when the extreme distal end portion 23 was rotated while contacting with the aorta wall, it rotated comparatively smoothly although an obstacle was felt a little. Further, the extreme distal end portion 23 was engaged substantially coaxially with the coronary artery opening. Particularly upon engagement with the right coronary artery opening, the extreme distal end portion 23 advanced to the interior of the right coronary artery.

As regards the working examples 1-3 and 1-4, the extreme distal end portion 23 rotated smoothly while contacting with the aorta wall. Further, the extreme distal end portion 23 contacted at the outer circumferential face thereof with the inner wall of the coronary artery opening.

As regards the working example 1-5, the extreme distal end portion 23 rotated smoothly while contacting with the aorta wall. Meanwhile, the extreme distal end portion 23 did not readily enter the coronary artery opening but the distal end collided with the coronary artery wall.

As regards the comparative example 1, the following result was obtained. In particular, the extreme distal end portion 78 engaged coaxially with the right coronary artery opening. In this state, the balloon catheter with a guide wire was inserted into the right coronary artery. In this instance, the user was able to operate the balloon catheter smoothly without a feel of an obstacle at all. Then, the extreme distal end portion 78 was disengaged from the right coronary artery opening and then the proximal end portion of the catheter 70 was rotated in the counterclockwise direction. Consequently, the extreme distal end portion 78 of the catheter 70 formed a substantially right angle with respect to the aorta wall and rotated while contacting with the aorta wall. At this time, resistance or an obstacle at the extreme distal end portion 78 of the catheter 70 was felt. The catheter 70 was further operated until the extreme distal end portion 78 was engaged in a coaxial state with the left coronary artery opening. In this state, the balloon catheter with a guide wire was inserted into the left coronary artery. Here, the user was able to operate the balloon catheter readily without a feel of an obstacle.

As described above, with the engaging method which uses the catheter 10 according to the embodiment of FIG. 1, when the target of engagement is changed over from one to the other of the left and right coronary artery openings 64 and 65, the extreme distal end portion 23 smoothly moves in a state in which it forms an angle less than a right angle with respect to the aorta wall 58a. Consequently, the extreme distal end portion 23 is less likely to damage the aorta wall 58a.

According to the result of the test described above, in the catheter 10 according to the embodiment of FIG. 1 wherein the intermediate portion 21 is formed substantially linearly, the angle defined by the extreme distal end portion 23 and the plane A can be set to be from 8 to 35°, and possibly set to be from 10 to 30°.

Method of Use of Catheter According to FIG. 13

As regards a method of use of the catheter 10a of FIG. 13, the following description is given. In particular, the extreme distal end portion 33 of the catheter 10a was engaged with the left coronary artery opening 64 first, and then the extreme distal end portion 33 was moved back to the proximity of the center of the aorta ascendens 58 and rotated to change over the target of engagement to the right coronary artery opening 65. However, similar to the case of the catheter 10 according to the embodiment of FIG. 1 as described hereinabove, in the catheter 10a according to the embodiment of FIG. 13, the extreme distal end portion 33 may be engaged with the coronary artery opening in accordance with the following procedure.

In particular, after the catheter 10a is introduced into the aorta ascendens 58 through the brachiocephalic artery 52, the extreme distal end portion 33 can be engaged with the right coronary artery opening 65, and then disengaged from the right coronary artery opening 65. Thereafter, the proximal end portion of the catheter 10a can be rotated in the counterclockwise direction. Consequently, the extreme distal end portion 33 rotates in the counterclockwise direction at a point of view at which the aorta valve side is viewed from the aorta ascendens 58 side. In this instance, while the extreme distal end portion 33 contacts with the aorta wall 58a, it smoothly moves in a state in which it forms an angle less than a right angle with respect to the aorta wall 58a. Consequently, the extreme distal end portion 33 rotates from the proximity of the right coronary artery opening 65 in such a manner as to pass the front side of the body of the patient until it reaches the proximity of the right coronary artery opening 65. Further, the extreme distal end portion 33 can be further rotated into engagement with the left coronary artery opening 64. It is to be noted that the engagement of the extreme distal end portion 33 with the left and right coronary artery openings 64 and 65 may be carried out in the order of the left coronary artery opening 64 and the right coronary artery opening 65 reversely to that described above.

If it is intended to achieve smoother movement of the extreme distal end portion 33 when the target of engagement is changed over from the right coronary artery opening 65 to the left coronary artery opening 64, then the extreme distal end portion 33 which has engaged with the right coronary artery opening 65 can be pulled back to the base end side once in the state shown in FIG. 5 to move the extreme distal end portion 33 away from the aorta wall. Thereafter, the extreme distal end portion 33 is rotated until it is directed to the left coronary artery opening 64 and then is brought into contact with a location of the patient displaced a little to the front side with respect to the left coronary artery opening 64 and then moved to the left coronary artery opening 64. On the other hand, if it is intended to achieve smoother movement of the extreme distal end portion 33 when the target of engagement is changed over from the left coronary artery opening 64 to the right coronary artery opening 65, the extreme distal end portion 33 which has engaged with the left coronary artery opening 64 is pulled back toward the proximal end side to the state of FIG. 5. Then, the extreme distal end portion 33 is rotated so as to be directed to the right coronary artery opening 65 and brought into contact with a location of the patient displaced a little to the rear side with respect to the right coronary artery opening 65 and then moved to the right coronary artery opening 65. In either case, the extreme distal end portion 33 smoothly moves in a state in which it forms an angle less than a right angle with respect to the aorta wall while it contacts at the outer circumferential face thereof with the aorta wall.

As apparent from the foregoing description, the catheter 10a can be configured such that the extreme distal end portion 33 can be engaged with one of the left coronary artery opening 64 and the right coronary artery opening 65, such that the extreme distal end portion 33 is disengaged from the one of the left coronary artery opening 64 and the right coronary artery opening 65, such that the extreme distal end portion 33 is rotated along the aorta wall 58a in a direction in which the extreme distal end portion 33 forms a smaller angle with respect to the aorta wall 58a, and such that the extreme distal end portion 33 is engaged with the other one of the left coronary artery opening 64 and the right coronary artery opening 65.

In order to confirm the operational characteristics and effects of the catheter 10a shown in FIG. 13 wherein the intermediate portion 31 is formed in a curved shape, a use test was carried out for working examples 2-1 to 2-5 among which the angle β is different and a comparative example 2 wherein the angle β is zero, which corresponds to a modification to the catheter 10a shown in FIG. 13 wherein the angle of the extreme distal end portion 33 with respect to the plane B is set to zero. In the test, the catheters of the working examples 2-1 to 2-5 and the comparative example 2 were inserted into a transparent model of the aorta and the coronary artery of the size of the original in water of 37° C. Then, the extreme distal end portion 33 was engaged with the right coronary artery opening. Thereafter, the extreme distal end portion 33 was disengaged from the right coronary artery opening and rotated in a direction corresponding to the direction indicated by arrow C in FIG. 17A until it was engaged with the left coronary artery opening. Results are indicated in Table 2 below.

TABLE 2

| | β | β' | β" | Inside the aorta | The degree of lesion inside the blood vessel Inside the coronary artery |
|---|---|---|---|---|---|
| Comparative Example 2 | 0 | 0 | 0 | serious | moderate |
| Example 2-1 | 7 | 11 | 3 | moderate | moderate |
| Example 2-2 | 11 | 17 | 6 | slight | Slight |
| Example 2-3 | 18 | 24 | 10 | slight | Slight |
| Example 2-4 | 29 | 41 | 14 | slight | slight |
| Example 2-5 | 36 | 52 | 22 | slight | moderate |

In Table 2, angle β is an angle at which the extreme distal end portion 33 projects three-dimensionally obliquely with respect to the plane B, which is a reference plane, shown in FIG. 13 in a natural state thereof, that is, in a state in which no external force acts upon the extreme distal end portion 33. The angle β' is an inclination angle of the extreme distal end portion 33 with respect to the plane B when the extreme distal end portion 33 moves along the aorta wall 58a. The angle β" is an angle at which a longitudinal axis of the extreme distal end portion 33 is inclined with respect to a longitudinal axial line of the coronary artery when the extreme distal end portion 33 is engaged with the coronary artery opening. The "slight," "moderate," and "serious" marks in Table 2 have the same meanings as those of the marks in Table 1.

With regard to the working examples 2-1 to 2-5 and the comparative example 2, substantially similar results to those of the working examples 1-1 to 1-5 and the comparative example 1 were obtained. Therefore, only an outline of the results is described.

As regards the working example 2-1, when the extreme distal end portion 33 rotated while contacting with the aorta wall, it rotated comparatively smoothly although an obstacle was felt a little. Further, the extreme distal end portion 33 was engaged substantially coaxially with the coronary artery opening. Particularly upon engagement with the right coronary artery opening, the extreme distal end portion 33 entered to the inside of the right coronary artery.

As regards the working example 2-2, although an obstacle was felt a little when the extreme distal end portion 33 rotated while contacting with the aorta wall, it rotated comparatively smoothly. Further, when the extreme distal end portion 33 was engaged with the coronary artery opening, it was positioned in the coronary artery opening, that is, in the coronary artery.

As regards the working examples 2-3 and 2-4, the extreme distal end portion 33 rotated smoothly while contacting with the aorta wall. Further, the extreme distal end portion 33 contacted at the outer circumferential face thereof with the inner wall of the coronary artery opening.

As regards the working example 2-5, the extreme distal end portion 33 rotated smoothly while contacting with the aorta wall. Further, the extreme distal end portion 33 was not able to enter the coronary artery opening and collided with the coronary artery wall.

As regards the comparative example 2, when the extreme distal end portion 33 rotated while contacting with the aorta wall such that it formed a substantially right angle with respect to the aorta wall, resistance or an obstacle was felt at the extreme distal end portion 33 of the catheter. Further, the extreme distal end portion 33 engaged in a coaxial state with the coronary artery opening, and entered the right coronary artery.

As described above, with the engaging method wherein the catheter 10a according to the embodiment of FIG. 12 is used, when the target of engagement is changed over from one to the other of the left and right coronary artery openings 64 and 65, the extreme distal end portion 33 can move smoothly in a state in which it forms an angle less than a right angle with respect to the aorta wall 58a. Therefore, the aorta wall 58a is less likely to be damaged.

According to the test results described above, in the catheter 10a according to the embodiment of FIG. 12 wherein the intermediate portion 31 is formed in a curved shape, the angle defined by the extreme distal end portion 33 and the plane A can be set to be from 7 to 36°, and possibly from 11 to 29°.

Various alternative materials and structures can be used without departing from the spirit and scope of the disclosed subject matter. For example, the method can include a clockwise turning of the catheter, and the extreme distal end portion can be obliquely angled out of a plane that contains the remaining portion of the catheter in a direction out of the paper when viewing either FIG. 2 or FIG. 13.

While some exemplary embodiments of the present invention have been described using specific terms, such description is for illustrative purpose only, and it is to be understood that changes and variations may be made without departing from the spirit or scope of the following claims. All conventional art references described above are herein incorporated in their entirety by reference.

What is claimed is:

1. A catheter for a coronary artery having a distal end configured to be introduced into an opening of a coronary artery from an artery of an arm, comprising:
    a catheter main body including a main body portion having a substantially linear shape in a natural state and a curved portion including a portion extending from the main body portion to the distal end and having a curved shape in a natural state;
    the curved portion including a first curve extending from the main body portion in a curved state, an intermediate portion extending from the first curve, a second curve extending from the intermediate portion and curved in a direction same as a direction of curvature of the first curve, and an extreme distal end portion having a substantially linear shape in a natural state extending from the second curve;
    the first curve, intermediate portion and second curve existing in a substantially same plane;
    the extreme distal end portion extending, when the curved portion is positioned on the upper side of the main body portion and is viewed from a point of view at which the curved portion is positioned on a right side of the main body portion, substantially linearly and obliquely out of the plane in which the first curve, intermediate portion and second curve exist, wherein the curved portion is shaped so as to be selectively engageable with an opening of a left coronary artery and an opening of a right coronary artery.

2. The catheter for a coronary artery according to claim 1, wherein, when the extreme distal end portion engages with the opening of the coronary artery, the first curve contacts with an inner wall of the aorta on a side opposite to the opening of the coronary artery, and a length over which the first curve and the inner wall of the aorta contact with each other is less than 10 mm.

3. The catheter for a coronary artery according to claim 1, wherein the curved portion is shaped such that, when the extreme distal end portion engages with the opening of the coronary artery, a longitudinal axial line of the opening of the coronary artery and a longitudinal axial line of the extreme distal end portion are inclined relative to each other.

4. The catheter for a coronary artery according to claim 1, wherein the curved portion consists of the first curve, intermediate portion, second curve and extreme distal end portion.

5. The catheter for a coronary artery according to claim 1, wherein the extreme distal end portion extends substantially linearly and obliquely out of the plane and away from a point of a viewer when the catheter is viewed from a point of view at which the curved portion is positioned on a right side and at a top of the main body portion.

6. The catheter for a coronary artery according to claim 1, wherein the catheter consists of:
    a hub portion, the hub portion continuously connecting with the main body portion, the main body portion having a substantially linear shape along an entire length of the main body portion;
    the main body portion which is continuously connected between the hub portion and the curved portion; and
    the curved portion, wherein the curved portion consists of the first curve, intermediate portion, second curve and extreme distal end portion, and wherein the first curve extends continuously from the main body portion.

7. A catheter configured to be engaged with an opening of a coronary artery, the catheter having a distal end configured to be introduced into the opening of the coronary artery from an artery of an arm, the catheter comprising:
    a catheter main body including a main body portion having a substantially linear shape in a natural state and a curved portion including a portion extending from the main body portion to the distal end and having a curved shape in a natural state;
    the curved portion including a first curve extending from the main body portion in a curved state, an intermediate portion extending from the first curve, a second curve extending from the intermediate portion and curved in a direction same as a direction of curvature of the first curve, and an extreme distal end portion having a substantially linear shape in a natural state extending from the second curve;
    the first curve, intermediate portion and second curve existing in a substantially same plane;
    the extreme distal end portion extending, when the curved portion is positioned on the upper side of the main body portion and is viewed from a point of view at which the curved portion is positioned on a right side of the main body portion, substantially linearly and obliquely out of the reference plane in which the first curve, intermediate portion and second curve exist;

the curved portion being shaped so as to be selectively engageable with an opening of a left coronary artery and an opening of a right coronary artery;

the catheter configured such that when the extreme distal end portion is engaged with one of the opening of the left coronary artery and the opening of the right coronary artery, that the extreme distal end portion is disengaged from the other one of the opening of the left coronary artery and the opening of the right coronary artery, and such that when the extreme distal end portion is engaged with one of the opening of the left coronary artery and the opening of the right coronary artery and the extreme distal end portion is rotated along a wall of the aorta in a direction in which the extreme distal end portion forms a smaller angle with respect to the wall of the aorta, that the extreme distal end portion becomes engaged with the other of the opening of the left coronary artery and the opening of the right coronary artery.

8. The catheter for a coronary artery according to claim 7, wherein the intermediate portion has a substantially linear shape, and the angle defined by the extreme distal end portion and the reference plane is from 8° to 35°.

9. The catheter for a coronary artery according to claim 7, wherein the intermediate portion has a substantially linear shape, and the angle defined by the extreme distal end portion and the reference plane is from 10° to 30°.

10. The catheter for a coronary artery according to claim 7, wherein the intermediate portion is shaped so as to be curved in a direction same as a direction of curvature of the first curve, and the angle defined by the extreme distal end portion and the reference plane is from 7° to 36°.

11. The catheter for a coronary artery according to claim 7, wherein the intermediate portion is shaped so as to be curved in a direction same as a direction of curvature of the first curve, and the angle defined by the extreme distal end portion and the reference plane is from 11° to 29°.

12. The catheter for a coronary artery according to claim 7, wherein the extreme distal end portion extends substantially linearly and obliquely out of the plane and away from a point of a viewer when the catheter is viewed from a point of view at which the curved portion is positioned on a right side and at a top of the main body portion.

13. The catheter for a coronary artery according to claim 7, wherein the catheter consists of:

a hub portion, the hub portion continuously connecting with the main body portion, the main body portion having a substantially linear shape along an entire length of the main body portion;

the main body portion which is continuously connected between the hub portion and the curved portion; and the curved portion, wherein the curved portion consists of the first curve, intermediate portion, second curve and extreme distal end portion, and wherein the first curve extends continuously from the main body portion.

14. A method for engaging a catheter for a coronary artery with an opening of the coronary artery, the catheter having a distal end configured to be introduced into the opening of the coronary artery from an artery of an arm, the catheter including a catheter main body having a main body portion with a substantially linear shape in a natural state and a curved portion extending from the main body portion to the distal end and having a curved shape in a natural state, the curved portion including a first curve extending from the main body portion in a curved state, an intermediate portion extending from the first curve, a second curve extending from the intermediate portion and curved in a direction same as a direction of curvature of the first curve, and an extreme distal end portion extending from the second curve and having a substantially linear shape in a natural state, the first curve, intermediate portion and second curve existing in a substantially same plane, the extreme distal end portion extending, when the curved portion is positioned on an upper side of the main body portion and is viewed from a point of view at which the curved portion is positioned on a right side of the main body portion, substantially linearly and at an oblique angle out of the reference plane in which the first curve, intermediate portion and second curve exist, the curved portion being shaped so as to be selectively engageable with an opening of the left coronary artery and an opening of the right coronary artery, the engaging method comprising:

engaging the extreme distal end portion with one of an opening of the left coronary artery and an opening of the right coronary artery;

disengaging the extreme distal end portion from the one of the opening of the left coronary artery and the opening of the right coronary artery;

rotating the extreme distal end portion along a wall of the aorta in a direction in which the extreme distal end portion forms a smaller angle with respect to the wall of the aorta; and engaging the extreme distal end portion with the other of the opening of the left coronary artery and the opening of the right coronary artery.

15. The method according to claim 14, wherein the intermediate portion has a substantially linear shape, and the angle defined by the extreme distal end portion and the reference plane is from 8° to 35°.

16. The method according to claim 14, wherein the intermediate portion has a substantially linear shape, and the angle defined by the extreme distal end portion and the reference plane is from 10° to 30°.

17. The method according to claim 14, wherein the intermediate portion is shaped so as to be curved in a direction same as a direction of curvature of the first curve, and the angle defined by the extreme distal end portion and the reference plane is from 7° to 36°.

18. The method according to claim 14, wherein the intermediate portion is shaped so as to be curved in a direction same as a direction of curvature of the first curve, and the angle defined by the extreme distal end portion and the reference plane is from 11° to 29°.

19. The method according to claim 14, wherein the extreme distal end portion extends substantially linearly and obliquely out of the plane and away from a point of a viewer when the catheter is viewed from a point of view at which the curved portion is positioned on a right side and at a top of the main body portion.

* * * * *